United States Patent
Aoki et al.

(10) Patent No.: US 10,184,913 B2
(45) Date of Patent: Jan. 22, 2019

(54) ABNORMALITY DIAGNOSIS SYSTEM OF A GAS SENSOR

(71) Applicant: TOYOTA JIDOSHA KABUSHIKI KAISHA, Toyota-shi, Aichi (JP)

(72) Inventors: Keiichiro Aoki, Sunto-gun (JP); Koji Ide, Gotenba (JP); Go Hayashita, Chigasaki (JP); Toyoharu Kaneko, Susono (JP); Tatsuhiro Hashida, Sunto-gun (JP); Kazuhiro Wakao, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 376 days.

(21) Appl. No.: 15/082,032

(22) Filed: Mar. 28, 2016

(65) Prior Publication Data
US 2016/0290961 A1    Oct. 6, 2016

(30) Foreign Application Priority Data
Apr. 2, 2015   (JP) ................... 2015-075567

(51) Int. Cl.
*G01N 27/407* (2006.01)
*G01N 27/417* (2006.01)
(Continued)

(52) U.S. Cl.
CPC ......... *G01N 27/4175* (2013.01); *F01N 11/00* (2013.01); *F02D 41/1454* (2013.01);
(Continued)

(58) Field of Classification Search
CPC ............. G01N 27/407; G01N 27/4074; G01N 33/0042; F01N 2560/027
See application file for complete search history.

(56) References Cited

U.S. PATENT DOCUMENTS 8,603,310 B2 * 12/2013 Ishida ................. G01N 27/419
123/703

FOREIGN PATENT DOCUMENTS

DE   10 2012 206 476 A1   10/2013
JP        61-128153        6/1986
(Continued)

*Primary Examiner* — Alexander S Noguerola
(74) *Attorney, Agent, or Firm* — Finnegan, Henderson, Farabow, Garrett & Dunner, LLP

(57) ABSTRACT

In a limited-current type gas sensor which detects oxygen-containing gas contained in an exhaust gas of an internal combustion engine, the decomposition current value of water ($H_2O$) may be detected, and existence of an abnormality of output characteristics of the sensor may be diagnosed based on its deviation from a reference decomposition current value of water corresponding to the concentration of water contained in the exhaust gas. A NOx sensor and a SOx sensor can also diagnose remarkable and minute abnormalities of output characteristics. In addition, the reference decomposition current value of water may be acquired based on the concentration of water detected by a separate humidity sensor or the decomposition current value of oxygen detected by the limited-current type gas sensor. The reference decomposition current value of water may be corrected based on a decomposition current value of oxygen detected during a fuel cut.

16 Claims, 10 Drawing Sheets

(51) Int. Cl.
  *G01N 33/00* (2006.01)
  *F02D 41/14* (2006.01)
  *F02D 41/22* (2006.01)
  *F01N 11/00* (2006.01)
  *G01N 27/406* (2006.01)
  *G01N 27/419* (2006.01)

(52) U.S. Cl.
  CPC ......... *F02D 41/1495* (2013.01); *F02D 41/22* (2013.01); *F02D 41/222* (2013.01); *G01N 27/407* (2013.01); *G01N 27/4074* (2013.01); *G01N 33/0042* (2013.01); *F01N 2550/00* (2013.01); *F01N 2560/02* (2013.01); *F01N 2560/025* (2013.01); *F01N 2560/026* (2013.01); *F01N 2560/027* (2013.01); *F01N 2900/0416* (2013.01); *G01N 27/4065* (2013.01); *G01N 27/4067* (2013.01); *G01N 27/4071* (2013.01); *G01N 27/419* (2013.01); *Y02T 10/40* (2013.01); *Y02T 10/47* (2013.01)

(56) References Cited

FOREIGN PATENT DOCUMENTS

| | | |
|---|---|---|
| JP | 2001-329904 | 11/2001 |
| JP | 2014-142199 A | 8/2014 |

\* cited by examiner

ABNORMALITY DIAGNOSIS SYSTEM OF A GAS SENSOR

This nonprovisional patent application is based on and claims the benefit of Japanese Patent Application No. 2015-075567, filed on Apr. 2, 2015, the entire contents of which are hereby incorporated by reference.

TECHNICAL FIELD

The present disclosure relates to an abnormality diagnosis system which diagnoses the existence of an abnormality in output characteristics of a gas sensor for detecting the concentration of an oxygen-containing gas in an exhaust gas (test gas) of an internal combustion engine.

BACKGROUND

In order to control an internal combustion engine, an air-fuel-ratio sensor (A/F sensor) which acquires the air-fuel ratio (A/F) of the fuel-air mixture in an combustion chamber based on the concentration of oxygen ($O_2$) contained in an exhaust gas has been used. One type of such an air-fuel-ratio sensor may be a limited-current type gas sensor.

A limited-current type gas sensor used as an air-fuel-ratio sensor may include a pumping cell which is an electrochemical cell containing a solid-electrolyte object with oxide ion conductivity and a pair of porous electrodes adhered to the surface of the solid-electrolyte object. One of the pair of the electrodes may be exposed to an exhaust gas of an internal combustion engine as a test gas introduced through a diffusion-resistance portion, and the other may be exposed to the atmosphere. Furthermore, when detecting an air-fuel ratio, the temperature of the above-mentioned solid-electrolyte object may be reaised to a predetermined temperature that is a temperature at which the solid-electrolyte object expresses oxide ion conductivity (henceforth, may be referred to as an "activation temperature") or higher.

In the above-mentioned state, when a voltage that is a voltage at which a decomposition of oxygen begins (decomposition starting voltage) or higher is applied between the above-mentioned one electrode as a cathode and the above-mentioned other electrode as an anode, oxygen contained in a test gas may be reductively decomposed at the cathode into an oxide ion ($O^{2-}$). This oxide ion may be conducted to the anode through the above-mentioned solid-electrolyte object to become oxygen, and can be discharged into the atmosphere. Such a migration of oxygen by conduction of an oxide ion through a solid-electrolyte object from a cathode side to an anode side can be referred to as an "oxygen pumping action."

By conduction of the oxide ion in association with the above-mentioned oxygen pumping action, current can flow between the above-mentioned pair of electrodes. Current which thus flows between a pair of electrodes may be referred to as "electrode current." This electrode current may have a tendency to become larger as the voltage applied between a pair of electrodes (henceforth, may be referred to simply as an "applied voltage") rises. However, since the flow rate of the test gas which arrives at the above-mentioned one electrode (cathode) is restricted by the diffusion-resistance portion, the consumption speed of oxygen in association with an oxygen pumping action may come to exceed the supply rate of oxygen to the cathode soon. Namely, the reductive decomposition of oxygen in the cathode can be in a diffusion-limited state.

In the above-mentioned diffusion-limited state, even though an applied voltage may be raised, electrode current may not increase, but may become approximately constant. Such property can be referred to as "limited-current property" and the range of applied voltage at which the limited-current property is expressed (observed) can be referred to as a "limited-current region." Furthermore, the electrode current in a limited-current region can be referred to as a "limited current", and the extent of a limited current (limited-current value) can correspond to the supply rate of oxygen to a cathode. Since the flow rate of a test gas which reaches the cathode as mentioned above may be maintained constant by the diffusion-resistance portion, the supply rate of oxygen to the cathode can correspond to the concentration of oxygen contained in the test gas.

Therefore, when an applied voltage is set to a "predetermined voltage within a limited-current region" in a limited-current type gas sensor used as an air-fuel-ratio sensor, electrode current (limited current) can correspond to the concentration of oxygen contained in a test gas. Thus, using the limited-current property of oxygen, the air-fuel-ratio sensor can detect the concentration of oxygen contained in an exhaust gas as a test gas, and the air-fuel ratio of the fuel-air mixture in a combustion chamber can be acquired based on it.

In a limited-current type sensor as mentioned above, for example, a crack and jam of a diffusion-resistance portion, a jam of a porous electrode, and a change in the conductivity of a solid electrolyte, etc. may cause an abnormality of output characteristics (for instance, an expansion of a detection value and shrinkage of a detection value, etc.). When the abnormality of output characteristics arises in a limited-current type sensor, it may become impossible to accurately detect the concentration of oxygen contained in an exhaust gas, and it can become impossible to accurately acquire an air-fuel ratio as an air-fuel-ratio sensor.

In an air-fuel-ratio sensor using a limited-current type gas sensor, for instance, a diagnostic method in which output characteristics of an air-fuel-ratio sensor is judged as abnormal when an output that deviates from a normal range of an output from the sensor corresponding to the range of an air-fuel-ratio control in an internal combustion engine is obtained from the sensor has been known.

However, an output from an air-fuel-ratio sensor may clamp within the above-mentioned normal range. In such a case, since the output from the sensor is contained in the above-mentioned normal range even though the output characteristics of the sensor have fallen into an abnormal state, there may be a problem that the sensor was wrongly judged as normal. In the art, a diagnostic method may judge that output characteristics of an air-fuel-ratio sensor is abnormal when the output from the sensor is held within the above-mentioned normal range for a predetermined time period or more during the execution of what is called "fuel cut (FC)" which cuts off the supply of fuel to an internal combustion engine (for instance, refer to the Patent Document 1 (PTL1)). In addition, the diagnostic method may be henceforth referred to as an "FC diagnosis."

CITATION LIST

Patent Literature

[PTL1] Japanese Patent Application Laid-Open (kokai) No. 2001-329904.

SUMMARY

An abnormality diagnosis of output characteristics of a limited-current type sensor according to the prior art as mentioned above may be performed based on the magnitude of a decomposition current of oxygen which exists in a comparatively large amount in an exhaust gas. Therefore, a large change in the output characteristics due to, for example, a crack and jam of a diffusion-resistance portion, etc. can be detected accurately and easily, but a minute change in the output characteristics due to, for example, a jam of a porous electrode, a change in the conductivity of a solid electrolyte, etc. cannot be detected accurately and easily.

Namely, in the diagnostic method in which output characteristics of an air-fuel-ratio sensor are judged as abnormal when an output that deviates from a normal range of an output from the sensor corresponding to the range of an air-fuel-ratio control in an internal combustion engine is obtained from the sensor, it may be difficult to detect a minute change in the output characteristics of the sensor even when a clamping phenomenon as mentioned above does not happen. Furthermore, also in a diagnostic method in which output characteristics of an air-fuel-ratio sensor is abnormal when the output from the sensor is held within the above-mentioned normal range for a predetermined time period or more during the execution of fuel cut (FC), it may be difficult to detect a minute change in the output characteristics of the sensor.

On the other hand, a limited-current property as mentioned above may not be limited only to oxygen. Specifically, among gases which contains an oxygen atom in its molecule (henceforth, may be referred to as an "oxygen-containing gas"), some gases can be reductively decomposed at a cathode and express limited-current property by properly choosing an applied voltage and the configuration of the cathode. As examples of such oxygen-containing gases, nitrogen oxide (NOx), sulfur oxide (SOx), water ($H_2O$), carbon dioxide ($CO_2$), etc. can be mentioned, for example.

Among the above oxygen-containing gas, when nitrogen oxide (NOx) and sulfur oxide (SOx) are contained in an exhaust gas from an internal combustion engine, there is a possibility to lead to problems, such as environmental pollution, deterioration and/or failure of a constituent member of an internal combustion engine, poisoning of an exhaust purification catalyst and the white smoke in an exhaust gas, for example. Then, in the art, an attempt to acquire the concentration of sulfur oxide and/or nitrogen oxide contained in an exhaust gas of an internal combustion engine by a limited-current type gas sensor using the above-mentioned oxygen pumping action, for instance, in order to change control of the internal combustion engine, to issue a warning about a failure of the internal combustion engine, or to use for an improvement of a self-diagnosis (OBD) of an exhaust purification catalyst has been made.

Since the concentrations of the nitrogen oxide (NOx) and sulfur oxide (SOx) contained in an exhaust gas may be small as compared with the concentration of oxygen ($O_2$) detected by an air-fuel-ratio sensor, high resolution (sensitivity) may be required for detecting nitrogen oxide and sulfur oxide. Therefore, since the detection accuracy of nitrogen oxide and sulfur oxide may fall sharply when an abnormality of output characteristics as mentioned above arises, it may be necessary to more strictly detect the existence of the abnormality of the output characteristics.

However, only a small amount (ppm level) of nitrogen oxide and sulfur oxide may exist in an exhaust gas, and a change in output characteristics of a decomposition current of nitrogen oxide and sulfur oxide in a limited-current type sensor may be minute, and therefore it can be difficult to detect such a minute change in the output characteristics based on a decomposition current of oxygen which exists in a large amount (% level) in an exhaust gas. Namely, it may be difficult to accurately diagnose the existence of an abnormality of output characteristics of a NOx sensor and a SOx sensor which detect the concentration of nitrogen oxide and sulfur oxide which exist only in a small amount (ppm level) in an exhaust gas, by a diagnostic method based on the decomposition current of oxygen as mentioned above.

Furthermore, since the above-mentioned FC diagnosis may require an execution of fuel cut (FC), there are the following problems that may occur, for example:

(a) The execution frequency of an abnormality diagnosis may be low (limited in an execution of FC).

(b) Since the concentration of oxygen contained in an exhaust gas during an execution of FC may be high, it may be necessary to raise the temperature of a sensor to a temperature (for instance, 750° C.) higher than the temperature (for instance, 600° C.) of the sensor at normal time (for instance, time when the air-fuel ratio is detected in a case where fuel is supplied an internal combustion engine and the air-fuel ratio is maintained near the stoichiometric ratio (theoretical air fuel ratio)), in order to express the limited-current property of oxygen. From a viewpoint of energy saving, it may not be desirable to thus raise the temperature of a sensor for an abnormality diagnosis.

(c) The limited current of high-concentration oxygen, which flows at a high sensor temperature as mentioned above may be larger than the limited current of oxygen at normal time (refer to the above). Therefore, it may be necessary to design a current-carrying member (for instance, a detector circuit, etc.) of a sensor which performs FC diagnosis so as to bear larger current than a current-carrying member of a sensor which does not perform FC diagnosis. As a result, it may be necessary to set up the rated current of the sensor which performs FC diagnosis larger than the rated current of the sensor which does not perform FC diagnosis. From a viewpoint of a manufacturing-cost saving, for example, it may not be desirable to raise the rated current of a sensor for an abnormality diagnosis.

As mentioned above, in the art, not only for an air-fuel-ratio sensor, but also for a NOx sensor and a SOx sensor, there may be a demand to a technology which can accurately and easily diagnose not only a remarkable abnormality of output characteristics, but also a minute abnormality.

Embodiments of the present disclosure may address a problem as mentioned above. Namely, embodiments of the present disclosure can accurately and easily diagnose not only a remarkable abnormality of output characteristics, but also a minute abnormality, not only for an air-fuel-ratio sensor, but also for a NOx sensor and a SOx sensor.

A decomposition current of water ($H_2O$), whose decomposition starts at an applied voltage higher than that for oxygen, can have a good correlation with output characteristics of an air-fuel-ratio sensor. FIG. 1 is a graph for showing a relation between an applied voltage and the electrode currents detected respectively by an air-fuel-ratio sensor having normal output characteristics and an air-fuel-ratio sensor having abnormal output characteristics when the air-fuel ratio of a fuel-air mixture supplied to an internal combustion engine is maintained at the stoichiometric ratio.

In FIG. 1, the solid line shows an electrode current in the air-fuel-ratio sensor which has normal output characteristics, the dashed line shows an electrode current in the air-fuel-ratio sensor which has abnormal output characteristics accompanied by an expansion of a detection value, and the dotted line shows an electrode current in the air-fuel-ratio sensor which has abnormal output characteristics accompanied by a shrinkage of a detection value. The above-mentioned "expansion of a detection value" refers to a phenomenon in which a detection value of an electrode current outputted from an air-fuel-ratio sensor becomes larger than its true value due to an abnormality of output characteristics, and the above-mentioned "shrinkage of a detection value" refers to a phenomenon in which a detection value of an electrode current outputted from an air-fuel-ratio sensor becomes smaller than its true value due to an abnormality of output characteristics.

As apparent from FIG. 1, at an applied voltage (about 0.6 V or more) at which the reductive decomposition of water at a cathode occurs, corresponding to the output characteristics of an air-fuel-ratio sensor, the detection value of electrode current is also expanded (dashed line) or is shrunk (dotted line) as compared with that at normal time (solid line). Namely, the magnitude of a decomposition current of water in an air-fuel-ratio sensor has a good correlation with the output characteristics of the air-fuel-ratio sensor. In addition, when the air-fuel ratio is maintained at the stoichiometric ratio, the concentration of oxygen contained in the exhaust gas comes to about 0 (zero). Therefore, in the graph of FIG. 1, the electrode current at an applied voltage (less than about 0.6 V) at which the reductive decomposition of water at a cathode does not occur is about 0 (zero).

Furthermore, the magnitude of a decomposition current of water may have a good correlation with output characteristics of an air-fuel-ratio sensor similar to the above, not only in an air-fuel-ratio sensor, but also in a NOx sensor and a SOx sensor. In addition, not only a large change in output characteristics, for example, due to a crack and jam of a diffusion-resistance portion, etc., but also a minute change in output characteristics, for example, due to a jam of a porous electrode and a change in the conductivity of a solid electrolyte, etc. can be detected accurately, according to the decomposition current of water.

Namely, not only a remarkable abnormality of output characteristics, but also minute abnormality thereof may be accurately and easily diagnosed based on the decomposition current of water, not only for an air-fuel-ratio sensor, but also for a NOx sensor and a SOx sensor.

More specifically, in a limited-current type gas sensor which detects an oxygen-containing gas contained in an exhaust gas of an internal combustion engine, the decomposition current of water ($H_2O$) whose decomposition starts at an applied voltage higher than that for oxygen ($O_2$) can be detected. And, based on the deviation of the detected decomposition current of water from a reference decomposition current of water corresponding to the concentration of water contained in the exhaust gas, the existence of an abnormality of output characteristics of the limited-current type gas sensor can be diagnosed. Thereby, not only a remarkable abnormality of output characteristics, but also a minute abnormality thereof can be accurately and easily diagnosed, not only for an air-fuel-ratio sensor, but also for a NOx sensor and a SOx sensor.

An abnormality diagnosis system of a gas sensor according to embodiments of the present disclosure will be explained below. A gas sensor to which embodiments of the present disclosure are applied may have the same configuration as a common limited-current type gas sensor. Specifically, the gas sensor to which embodiments of the present disclosure are applied may comprise an element portion, a heater, a voltage-control portion, a temperature adjustment portion and a measurement control portion.

The element portion may comprise a first electrochemical cell including a solid-electrolyte object with oxide ion conductivity and a first electrode and second electrode respectively formed on the surface of the solid-electrolyte object, a compact object and a diffusion-resistance portion. Furthermore, the element portion may be configured so that an exhaust gas of an internal combustion engine as a test gas is introduced into an interior space defined by said solid-electrolyte object and said compact object and said diffusion-resistance portion through said diffusion-resistance portion. In addition, the element portion may be configured so that said first electrode is exposed to said interior space and said second electrode is exposed to a first another space which is a space other than said interior space.

The heater may generate heat for heating said element portion when energized.

The voltage-control portion may change a first applied voltage that is a voltage applied between said first electrode and said second electrode.

The temperature adjustment portion may change the temperature of said element portion by controlling the amount of energization to said heater.

The measurement control portion may control said first applied voltage using said voltage-control portion, control the temperature of said element portion using said temperature adjustment portion, and acquire a first electrode current value that is a value of a current flowing between said first electrode and said second electrode.

Said first electrode may be configured to be able to decompose water ($H_2O$) contained in said test gas, in a first state, and to be able to decompose a test component which can be a component containing an oxygen atom in its molecular structure and contained in said test gas, in a second state. As will be mentioned later in detail, such a first electrode can be manufactured according to a component to be decomposed, for instance, by suitably choosing a material and structure, etc. of the electrode. Specifically, a test component can refer to at least one of oxygen ($O_2$), nitrogen oxide (NOx) and the sulfur oxide (SOx).

The first state can be a state where the temperature of said element portion is a first predetermined temperature which may be a temperature not lower than an activation temperature that may be a temperature at which said solid-electrolyte object expresses oxide ion conductivity and said first applied voltage is a first predetermined voltage falling within a predetermined first voltage zone. Namely, the first voltage zone can be a range of voltage not lower than a voltage at which the decomposition of water begins (decomposition starting voltage). As will be mentioned later in detail, a concrete value of the first predetermined voltage can be defined suitably as a voltage at which water contained in the test gas is decomposed at the first electrode and a current flowing between the first electrode and the second electrode due to the decomposition of water can be detected by the measurement control portion, in a state that the temperature of the element portion is the first predetermined temperature.

The second state can be a state where the temperature of said element portion is said first predetermined temperature and said first applied voltage is a second predetermined voltage falling within a predetermined second voltage zone. Namely, the second voltage zone may be a range of voltage not lower than a voltage at which the decomposition of the test component begins (decomposition starting voltage). As will be mentioned later in detail, a concrete value of the second predetermined voltage can be defined suitably, depending the sort of the test component, as a voltage at which the test component contained in the test gas is decomposed at the first electrode and a current flowing between the first electrode and a second electrode due to the decomposition of the test component can be detected by the measurement control portion, in a state that the temperature of the element portion is the first predetermined temperature.

Furthermore, said measurement control portion may be configured to acquire said first electrode current value acquired in said second state as a test component concentration-related value which is a value associated with the concentration of said test component contained in said test gas. Based on the test component concentration-related value thus acquired, the concentration of the test component which may be an oxygen-containing gas which contains an oxygen atom in its molecular structure (especially, at least one of oxygen ($O_2$), nitrogen oxide (NOx) and sulfur oxide (SOx)) can be acquired. Embodiments of the present disclosure may be an abnormality diagnosis system for a gas sensor which diagnoses whether the output characteristics of such a gas sensor is abnormal or not.

In addition, the first electrode current detected in the second state may include an electrode current resulting from the decomposition of the test component. However, this first electrode current may also include an electrode current resulting from the decomposition of oxygen-containing gas other than the test component whose concentration in the test gas is to be detected. In this case, in order to acquire the concentration of the test component in the test gas based on the test component concentration-related value, for example, a treatment such as elimination of an influence from the electrode current resulting from the decomposition of the oxygen-containing gas other than the test component. etc. may be needed.

In embodiments of the present disclosure, said measurement control portion may have previously memorized a first correspondence relation that is a correspondence relation of a moisture-related value with a reference water decomposition current value. The moisture-related value may be a value corresponding to the concentration of water contained in said test gas. Specifically, the moisture-related value may be the concentration of water contained in a test gas, or a value, such as a physical-property value or quantity of state, which changes corresponding to the concentration of water, for example. As an example of such a value, for example, the concentration of water contained in the test gas detected by a humidity sensor disposed in an exhaust-gas pathway of the internal combustion engine can be mentioned. Alternatively, as another example of such a value, for example, a value of a current which flows between the electrodes of the electrochemical cell due to the decomposition of oxygen contained in the test gas when fuel is supplied to the internal combustion engine and a voltage at which oxygen can be decomposed is applied between the electrodes can be mentioned. The value of this current may change corresponding to the air-fuel ratio of the fuel-air mixture supplied to the internal combustion engine. An air-fuel ratio can affect the concentration of water contained in the test gas. Therefore, the value of this current can be used as the moisture-related value.

The reference water decomposition current value is a value of a current flowing between said first electrode and said second electrode due to the decomposition of water contained in said gas when said first electrochemical cell of said gas sensor in a normal state is in said first state. Therefore, the first correspondence relation can be acquired by measuring values of currents flowing between the first electrode and the second electrode due to the decomposition of water contained in the test gas at various moisture-related values, in the first electrochemical cell of the gas sensor which is in a normal state, for example.

In addition, for example, the acquired first correspondence relation can be stored as a data table (for instance, a data map, etc.) which shows the correspondence relation in a data storage device (for instance, ROM, etc.) which an ECU (Electronic Control Unit) comprises, and can be referred to by a CPU (Central Processing Unit) in an abnormality diagnosis of output characteristics of the gas sensor.

Namely, based on the above-mentioned first correspondence relation, the measurement control portion can specify a value of a current which will flow between the first electrode and the second electrode due to the decomposition of water contained in the test gas when the gas sensor is normal and the first electrochemical cell is in the first state, from the moisture-related value acquired at a certain point in time. Therefore, when deviation between the value of the current thus specified and the value of the current which actually flows between the first electrode and the second electrode due to the decomposition of water contained in the test gas in the first state is large, it can be judged that the output characteristics of the gas sensor is abnormal.

Then, said measurement control portion can be configured to perform the following treatments, when fuel is supplied to said internal combustion engine:

(1) acquire said moisture-related value at present, (2) specify a reference water decomposition current value corresponding to said acquired moisture-related value, based on said first correspondence relation, and (3) acquire a water decomposition current value which is a value of a current flowing between said first electrode and said second electrode due to the decomposition of water contained in said test gas, based on said first electrode current value acquired in said first state.

And, said measurement control portion can be configured to judge that said gas sensor is abnormal, when a moisture detection deviation, which is a ratio of a value obtained by subtracting said specified reference water decomposition current value from said water decomposition current value to said specified reference water decomposition current value, is larger than a predetermined first upper limit, or when said moisture detection deviation is smaller than a predetermined first lower limit. In addition, the concrete values of the above-mentioned first upper limit and first lower limit can be suitably defined according to the magnitude of a detection error of the concentration of the test component permitted in the use of the gas sensor to which embodiments of the present disclosure are applied, for example.

In accordance with embodiments of the present disclosure, in a limited-current type gas sensor which detects an oxygen-containing gas contained in an exhaust gas of an internal combustion engine, a decomposition current of water ($H_2O$) whose decomposition starts at an applied voltage higher than that for oxygen ($O_2$) is detected. And, based on the deviation of the decomposition current of water detected as mentioned above from a reference decomposition current of water corresponding to the concentration of water contained in the exhaust gas, the existence of an abnormality of output characteristics of the limited-current type gas sensor can be diagnosed. Thereby, not only in an air-fuel-ratio sensor that detects a decomposition current of oxygen which exists in a large amount (% level) in an exhaust gas, but also in a NOx sensor and SOx sensor which detect the nitrogen oxide and sulfur oxide which exist only in a small amount (ppm level) in an exhaust gas, not only a remarkable abnormality of output characteristics, but also a minute abnormality thereof can be diagnosed accurately.

Furthermore, an abnormality diagnosis of output characteristics of a gas sensor in accordance with embodiments of the present disclosure may be performed when fuel is supplied to an internal combustion engine. Therefore, problems resulting from the execution of a fuel cut (FC) as shown in the above-mentioned (a) to (c) may not accompany the abnormality diagnosis of output characteristics of a gas sensor in accordance with embodiments of the present disclosure. Namely, in accordance with embodiments of the present disclosure, an abnormality diagnosis of output characteristics of a gas sensor can be performed in a usual operating state of an internal combustion engine (namely, state not during the execution of FC), without raising the temperature of the sensor or raising the rated current of the sensor for an abnormality diagnosis. When the air-fuel ratio of the fuel-air mixture supplied to the internal combustion engine is maintained at the stoichiometric ratio, since the concentration of oxygen contained in an exhaust gas can become about 0 (zero) as mentioned above referring to FIG. 1, the decomposition current of water can be detected.

In accordance embodiments of the present disclosure, not only in an air-fuel-ratio sensor, but also in a NOx sensor and a SOx sensor, not only a remarkable abnormality of output characteristics, but also a minute abnormality thereof can be diagnosed accurately and easily.

Embodiments of the present disclosure can be applied to a limited-current type gas sensor. As examples of a limited-current type sensor, an air-fuel-ratio sensor ($O_2$ sensor), a NOx sensor and a SOx sensor can be mentioned, for example. Namely, the embodiments of the present disclosure can be applied to an air-fuel-ratio sensor ($O_2$ sensor).

When embodiments of the present disclosure are applied to an air-fuel-ratio sensor, said first electrode can be configured to be able to decompose oxygen as said test component contained in said test gas in said second state where said first applied voltage is in said second voltage zone lower than said first voltage zone. Furthermore, said measurement control portion may be configured to acquire a first oxygen decomposition current value which is a value of a current flowing between said first electrode and said second electrode due to the decomposition of oxygen contained in said test gas, based on said test component concentration-related value acquired in said second state where said first applied voltage is in said second voltage zone lower than said first voltage zone.

In this case, the gas sensor to which embodiments of the present disclosure are applied may be an $O_2$ sensor or air-fuel-ratio sensor which detects the concentration of oxygen contained in the exhaust gas and/or the air-fuel ratio of a fuel-air mixture supplied to the internal combustion engine, based on the first electrode current detected in the second state. Therefore, the material and structure of the first electrode may be chosen so that oxygen contained in the test gas can be decomposed in the second state. Furthermore, the second predetermined voltage may be set to a voltage at which the first electrode as mentioned above can reductively decompose oxygen contained in the test gas, in a state where the temperature of the element portion is the first predetermined temperature.

Also when embodiments of the present disclosure are applied to an air-fuel-ratio sensor ($O_2$ sensor) as mentioned above, the measurement control portion may acquire the moisture-related value at present, and specify the reference water decomposition current value corresponding to the acquired moisture-related value based on the first correspondence relation, following the above-mentioned procedures (1) to (3). On the other hand, the measurement control portion may acquire the water decomposition current value which is a value of a current which flows between the first electrode and the second electrode due to the decomposition of water contained in the test gas, based on the first electrode current value detected in the first state. And, the measurement control portion may judge whether the output characteristics of the gas sensor are abnormal, based on the moisture detection deviation, which can be a ratio of a value obtained by subtracting the specified reference water decomposition current value from the acquired water decomposition current value to the reference water decomposition current value specified as mentioned above.

As mentioned above, when fuel is supplied to the internal combustion engine, the concentration of water contained in the test gas detected by the humidity sensor disposed in the exhaust-gas pathway of the internal combustion engine, for example, can be used as the above-mentioned moisture-related value.

Therefore, when embodiments of the present disclosure are applied to an air-fuel-ratio sensor ($O_2$ sensor) as mentioned above, said measurement control portion may further comprise a humidity sensor which detects the concentration of water contained in said test gas. In addition, said measurement control portion may be configured to acquire said detected concentration of water as said moisture-related value. In this case, said measurement control portion may have previously memorized said first correspondence relation in which the concentration of water detected by said humidity sensor is used as said moisture-related value. In accordance with this, the measurement control portion can specify the reference water decomposition current value from the detected concentration of water, based on the first correspondence relation.

By the way, as mentioned above, when fuel is supplied to the internal combustion engine and a voltage at which oxygen can be decomposed is applied between the electrodes of the electrochemical cell, the value of the current which flows between these electrodes due to the decomposition of oxygen contained in the test gas can be used as the above-mentioned moisture-related value.

Therefore, when embodiments of the present disclosure are applied to an air-fuel-ratio sensor ($O_2$ sensor) as mentioned above, said measurement control portion may be configured to acquire said acquired first oxygen decomposition current value as said moisture-related value. In this case, said measurement control portion may have previously memorized said first correspondence relation in which said first oxygen decomposition current value acquired when said first electrochemical cell of said gas sensor in a normal state is in said second state is used as said moisture-related value. Based on this first correspondence relation, the measurement control portion can specify the reference water decomposition current value from the acquired first oxygen decomposition current value.

However, when the output characteristics of the gas sensor is already in an abnormal state, the acquired first oxygen decomposition current value may be inaccurate, and the reference water decomposition current value specified as a result may be inaccurate. It may be difficult to perform an accurate abnormality diagnosis of the output characteristics of the gas sensor in accordance with an abnormality judgment based on such an inaccurate reference water decomposition current value.

Then, when the reference water decomposition current value is specified from the first oxygen decomposition current value as mentioned above, it may be desirable to diagnose whether the output characteristics of the gas sensor is in an abnormal state using some sort of an index, and to correct the reference water decomposition current value specified as mentioned above, according to the change in the output characteristics of the gas sensor from that in a normal state, when judged that the output characteristics of the gas sensor is in an abnormal state.

As the above-mentioned "index", for example, the value of a current which flows between the first electrode and the second electrode due to the decomposition of oxygen contained in the test gas when fuel is not supplied to the internal combustion engine can be used. In other words, using the same technique as the above-mentioned FC diagnosis, the change in the output characteristics of the gas sensor from that in a normal state can be detected, and the reference water decomposition current value can be corrected according to this change.

In the above-mentioned case, said measurement control portion may need to have previously memorized a first reference atmosphere decomposition current value which is a value of a current flowing between said first electrode and said second electrode due to the decomposition of oxygen contained in said test gas when fuel is not supplied to said internal combustion engine and said first electrochemical cell of said gas sensor in a normal state is in said second state.

The first reference atmosphere decomposition current value can be acquired by measuring a value of a current which flows between the first electrode and the second electrode due to the decomposition of oxygen contained in the test gas when fuel is not supplied to the internal combustion engine, in the first electrochemical cell of the gas sensor in a normal state, for example. In addition, the acquired first reference atmosphere decomposition current value can be stored in a data storage device (for instance, ROM, etc.) which an ECU comprises, and can be referred to by a CPU in an abnormality diagnosis of output characteristics of the gas sensor, for example.

Furthermore, said measurement control portion may be configured to acquire the first atmosphere decomposition current value which is a value of a current flowing between said first electrode and said second electrode due to the decomposition of oxygen contained in said test gas, based on said first electrode current value acquired in said second state when fuel is not supplied to said internal combustion engine. When the gas sensor is in a normal state, the first atmosphere decomposition current value thus acquired and the previously memorized first reference atmosphere decomposition current value may need to be identical. On the other hand, when the output characteristics of the gas sensor is in an abnormal state, the first atmosphere decomposition current value deviates from the first reference atmosphere decomposition current value, according to the change in the output characteristics of the gas sensor from that in a normal state.

Then, said measurement control portion may be configured to correct said specified reference water decomposition current value based on a ratio of said acquired first atmosphere decomposition current value to said first reference atmosphere decomposition current value. Thereby, even if the output characteristics of the gas sensor is already in an abnormal state when the reference water decomposition current value is specified based on the first correspondence relation from the first oxygen decomposition current value acquired as mentioned above, the reference water decomposition current value can be corrected based on the first atmosphere decomposition current value acquired separately. As a result, even if the output characteristics of the gas sensor is already in an abnormal state, the abnormality diagnosis of the output characteristics of the gas sensor can be performed accurately.

However, in order to acquire the above-mentioned first atmosphere decomposition current value, an execution of a fuel cut (FC) may be required like an abnormality diagnosis according to the above-mentioned conventional technology. Therefore, in this case, problems such as the above-mentioned (a) to (c) may not be eliminated. However, also in this case, based on the decomposition current of water whose decomposition starts in an applied voltage higher than that for oxygen, the existence of an abnormality of the output characteristics of the gas sensor may be diagnosed. Therefore, also in this case, an abnormality of the output characteristics of the gas sensor can be diagnosed accurately.

In the above-mentioned case, the measurement control portion can correct the specified reference water decomposition current value based on the ratio of the first atmosphere decomposition current value to the first reference atmosphere decomposition current value acquired by the same technique as the above-mentioned FC diagnosis. However, when the change in the output characteristics of the gas sensor from that in a normal state is excessive and the first atmosphere decomposition current value has remarkably deviated from the first reference atmosphere decomposition current value, the output characteristics of the gas sensor may be abnormal, without correcting the reference water decomposition current value as mentioned above in order to more strictly detect the existence of an abnormality of the output characteristics of the gas sensor based on the first atmosphere decomposition current value.

Then, said measurement control portion may be configured to judge that said gas sensor is abnormal, when a first atmosphere detection deviation, which is a ratio of a value obtained by subtracting said first reference atmosphere decomposition current value from said acquired first atmosphere decomposition current value to said first reference atmosphere decomposition current, is larger than a predetermined second upper limit, or when said first atmosphere detection deviation is smaller than a predetermined second lower limit. In addition, the concrete values of the above-mentioned second upper limit and second lower limit can be suitably defined according to the magnitude of a detection error of the concentration of the test component permitted in the use of the gas sensor to which the embodiments of the present disclosure are applied, for example.

In accordance with the above, when the first atmosphere detection deviation deviates from a range determined by the predetermined second upper limit and second lower limit, it may be immediately judged that the output characteristics of the gas sensor is abnormal. Namely, in the above-mentioned case, there may be no need to correct the reference water decomposition current value based on the ratio of the first atmosphere decomposition current value to the first reference atmosphere decomposition current value in order to perform the abnormality diagnosis of the output characteristics of the gas sensor based on the water decomposition current value. Therefore, the existence of an abnormality of the output characteristics of the gas sensor can be judged quickly and simply.

By the way, embodiments of the present disclosure can be applied to a limited-current type gas sensor. As examples of a limited-current type sensor, an air-fuel-ratio sensor ($O_2$ sensor), a NOx sensor and a SOx sensor can be mentioned, for example. Namely, embodiments of the present disclosure can be applied to a NOx sensor and a SOx sensor.

When embodiments of the present disclosure are applied to a NOx sensor, said first electrode may be configured to be able to decompose nitrogen oxide as said test component contained in said test gas in said second state where said first applied voltage is in said second voltage zone lower than said first voltage zone. Furthermore, said measurement control portion may be configured to acquire a NOx decomposition current value which is a value of a current flowing between said first electrode and said second electrode due to the decomposition of nitrogen oxide contained in said test gas, based on said test component concentration-related value acquired in said second state where said first applied voltage is in said second voltage zone lower than said first voltage zone.

In this case, the gas sensor to which embodiments of the present disclosure are applied may be a NOx sensor which detects the concentration of nitrogen oxide contained in the exhaust gas based on the first electrode current detected in the second state. Therefore, the material and structure of the first electrode can be chosen so that nitrogen oxide contained in the test gas can be decomposed in the second state where the first applied voltage is in the second voltage zone lower than the first voltage zone. Furthermore, the second predetermined voltage may be set to a voltage at which the first electrode as mentioned above can reductively decompose nitrogen oxide contained in the test gas, in a state where the temperature of the element portion is the first predetermined temperature.

By the way, as mentioned above, the amount of oxygen contained in an exhaust gas may be large (% level), while the amount of nitrogen oxide contained in an exhaust gas may be very slight (ppm level). On the other hand, the decomposition starting voltage of oxygen may be almost equal to the decomposition starting voltage of nitrogen oxide. Therefore, the first electrode which may be configured so that nitrogen oxide contained in the test gas can be decomposed in the second state as mentioned above can also decompose oxygen.

Therefore, when the exhaust gas from the internal combustion engine is introduced into the interior space of the element portion as it is and is contacted with the first electrode that is a cathode of the first electrochemical cell, the proportion of a current resulting from the reductive decomposition of oxygen in a current which flows between the first electrode and the second electrode may become remarkably larger as compared with the proportion of a current resulting from the reductive decomposition of nitrogen oxide. Under such a situation, it may be difficult to accurately detect the current resulting from the reductive decomposition of nitrogen oxide, and to accurately detect the concentration of nitrogen oxide contained in the exhaust gas.

A pump cell which reductively decomposes oxygen contained in a test gas and discharges the same outside can be disposed on the upstream side of a sensor cell which detects an electrode current corresponding to the concentration of nitrogen oxide contained in the test gas to eliminate the influence of oxygen to the electrode current detected by the sensor cell, and can be applied also to a NOx sensor to which the embodiments of the present disclosure are applied.

In this case, said element portion may further comprise a second electrochemical cell including said solid-electrolyte object or another solid-electrolyte object other than said solid-electrolyte object and a third electrode and fourth electrode respectively formed on the surface of the solid-electrolyte object. The second electrochemical cell may be configured so that said third electrode is exposed to said interior space and said fourth electrode is exposed to a second another space which is a space other than said interior space. Furthermore, said third electrode may be formed in a location nearer to said diffusion-resistance portion than said first electrode. In addition, said voltage-control portion may be configured also to apply a second applied voltage between said third electrode and said fourth electrode.

Said third electrode can be configured to be able to decompose oxygen contained in said test gas in a third state, and to discharge the oxygen from said interior space. As will be mentioned later in detail, such a third electrode can be manufactured by suitably choosing a material and structure, etc. of the electrode, for example.

The third state may be a state where the temperature of said element portion is said first predetermined temperature and said second applied voltage is applied. A concrete value of the second applied voltage can be suitably defined as a voltage at which oxygen contained in the test gas can be decomposed at the third electrode and the limited-current property of oxygen can be expressed.

In accordance with the above, oxygen contained in the test gas and introduced into the interior space of the element portion may be decomposed by the second electrochemical cell as a pump cell disposed on the upstream side, and is discharged from the interior space. As a result, the concentration of oxygen contained in the test gas and has arrived at the first electrode that is a cathode of the first electrochemical cell may be substantially 0 (zero), or be extremely low. For this reason, the proportion of the current resulting from a reductive decomposition of oxygen in the current which flows between the first electrode and the second electrode may also be substantially 0 (zero) or very low. In other words, the test component concentration-related value may be equal or almost equal to the value of the current resulting from the reductive decomposition of nitrogen oxide. Therefore, the test component concentration-related value may be acquired as the NOx decomposition current value. Thus, the current resulting from the reductive decomposition of nitrogen oxide contained in a quite slight amount (ppm level) in the exhaust gas can be accurately detected, and the concentration of nitrogen oxide contained in the exhaust gas can be accurately detected.

On the other hand, when embodiments of the present disclosure are applied to a SOx sensor, said first electrode may be configured to be able to decompose sulfur oxide as said test component contained in said test gas in said second state. Furthermore, said measurement control portion may be configured to acquire a SOx decomposition current value which is a value of a current flowing between said first electrode and said second electrode due to the decomposition of sulfur oxide contained in said test gas, based on said test component concentration-related value acquired in said second state.

In this case, the gas sensor to which the embodiments of the present disclosure are applied may be a SOx sensor which detects the concentration of sulfur oxide contained in the exhaust gas based on the first electrode current detected in the second state. Therefore, the material and structure of the first electrode may be chosen so that sulfur oxide contained in the test gas can be decomposed in the second state. Furthermore, the second predetermined voltage may be set to a voltage at which the first electrode as mentioned above can reductively decompose sulfur oxide contained in the test gas, in a state where the temperature of the element portion is the first predetermined temperature.

By the way, as mentioned above, the amount of oxygen contained in an exhaust gas may be large (% level), while the amount of sulfur oxide contained in an exhaust gas may be very slight (ppm level). On the other hand, the decomposition starting voltage of oxygen may be almost equal to the decomposition starting voltage of sulfur oxide. Therefore, the first electrode which can be configured so that sulfur oxide contained in the test gas can be decomposed in the second state as mentioned above can also decompose oxygen.

Therefore, when the exhaust gas from the internal combustion engine is introduced into the interior space of the element portion as it is and is contacted with the first electrode that is a cathode of the first electrochemical cell, the proportion of a current resulting from the reductive decomposition of oxygen in a current which flows between the first electrode and the second electrode may become remarkably larger as compared with the proportion of a current resulting from the reductive decomposition of sulfur oxide. Under such a situation, it may be difficult to accurately detect the current resulting from the reductive decomposition of sulfur oxide, and to accurately detect the concentration of sulfur oxide contained in the exhaust gas.

A pump cell which reductively decomposes oxygen contained in a test gas and discharges the same outside can be disposed on the upstream side of a sensor cell which detects an electrode current corresponding to the concentration of sulfur oxide contained in the test gas to eliminate the influence of oxygen to the electrode current detected by the sensor cell has been known, and can be applied also to a SOx sensor to which embodiments of the present disclosure are applied.

In this case, said element portion may further comprise a second electrochemical cell including said solid-electrolyte object or another solid-electrolyte object other than said solid-electrolyte object and a third electrode and fourth electrode respectively formed on the surface of the solid-electrolyte object. The second electrochemical cell may be configured so that said third electrode is exposed to said interior space and said fourth electrode is exposed to a second another space which is a space other than said interior space. Furthermore, said third electrode may be formed in a location nearer to said diffusion-resistance portion than said first electrode. In addition, said voltage-control portion may be configured also to apply a second applied voltage between said third electrode and said fourth electrode.

Said third electrode may be configured to be able to decompose oxygen contained in said test gas in a third state, and to discharge the oxygen from said interior space. As will be mentioned later in detail, such a third electrode can be manufactured by suitably choosing a material and structure, etc. of the electrode, for example.

The third state may be a state where the temperature of said element portion is said first predetermined temperature and said second applied voltage is applied. A concrete value of the second applied voltage can be suitably defined as a voltage at which oxygen contained in the test gas can be decomposed at the third electrode and the limited-current property of oxygen can be expressed.

In accordance with the above, oxygen contained in the test gas introduced into the interior space of the element portion may be decomposed by the second electrochemical cell as a pump cell disposed on the upstream side of the first electrochemical cell as a sensor cell, and may be discharged from the interior space. As a result, the concentration of oxygen contained in the test gas which has arrived at the first electrode that is a cathode of the first electrochemical cell may be substantially 0 (zero), or may be extremely low. For this reason, the proportion of the current resulting from a reductive decomposition of oxygen in the current which flows between the first electrode and the second electrode may also be substantially 0 (zero) or very low. In other words, the test component concentration-related value may be equal or almost equal to the value of the current resulting from the reductive decomposition of sulfur oxide. Therefore, the test component concentration-related value may be acquired as the SOx decomposition current value. Thus, the current resulting from the reductive decomposition of sulfur oxide contained in a quite slight amount (ppm level) in the exhaust gas can be accurately detected, and the concentration of sulfur oxide contained in the exhaust gas can be accurately detected.

By setting the second predetermined voltage in the second state to a voltage at which not only sulfur oxide, but also water contained in the test gas can be decomposed, the detection value relevant to the concentration of sulfur oxide contained in the test gas based on a change of the decomposition current of water in the sensor can be also acquired. The above-mentioned "change of the decomposition current of water" may be a deviation of the magnitude of the electrode current from a predetermined standard value at a predetermined applied voltage at which the reductive decomposition of water occurs, for example. In this case, the predetermined standard value may be an electrode current corresponding to the concentration of water contained in the test gas at the point in time, in a case where the sensor is not affected by the influence in association with the reductive decomposition of sulfur oxide.

Alternatively, the above-mentioned "change of the decomposition current of water" may be a difference between an electrode current detected when the applied voltage is being increasingly swept (being increased gradually) and an electrode current detected when the applied voltage is being decreasingly swept (being decreased gradually) in a predetermined voltage zone which includes the second predetermined voltage in the above-mentioned second state, for example. In this case, for example, a correspondence relation between this difference and the concentration of sulfur oxide contained in the test gas can have been previously obtained and, thereby, the concentration of sulfur oxide can be specified from this difference.

Although the concentration of sulfur oxide contained in the test gas can be acquired by various techniques including the above-mentioned various techniques, an abnormality of the output characteristics of a gas sensor can be detected accurately and easily in accordance with embodiments of the present disclosure, whichever technique is adopted.

As mentioned above, when fuel is supplied to the internal combustion engine, the concentration of water contained in the test gas detected by the humidity sensor disposed in the exhaust-gas pathway of the internal combustion engine, for example, can be used as the above-mentioned moisture-related value.

Therefore, when embodiments of the present disclosure are applied to a NOx sensor or a SOx sensor as mentioned above, said measurement control portion may further comprise a humidity sensor which may detect the concentration of water contained in said test gas. In addition, said measurement control portion may be configured to acquire said detected concentration of water as said moisture-related value. In this case, said measurement control portion may have previously memorized said first correspondence relation in which the concentration of water detected by said humidity sensor is used as said moisture-related value. In accordance with this, the measurement control portion can specify the reference water decomposition current value from the detected concentration of water, based on the first correspondence relation.

As mentioned above, when fuel is supplied to the internal combustion engine and a voltage at which oxygen can be decomposed is applied between the electrodes of the electrochemical cell, the value of the current which flows between these electrodes due to the decomposition of oxygen contained in the test gas can be used as the above-mentioned moisture-related value. When embodiments of the present disclosure are applied to a two-cell type NOx sensor or SOx sensor which comprises a pump cell as mentioned above, the value of the decomposition current of oxygen which flows between the electrodes of the pump cell can be used as the above-mentioned moisture-related value.

Therefore, when embodiments of the present disclosure are applied to a two-cell type NOx sensor or SOx sensor which comprises a pump cell as mentioned above, said measurement control portion may be configured to acquire a second oxygen decomposition current value which is a value of a current flowing between said third electrode and said fourth electrode due to the decomposition of oxygen contained in said test gas in said third state and to acquire said acquired second oxygen decomposition current value as said moisture-related value. In this case, said measurement control portion may have previously memorized said first correspondence relation in which said second oxygen decomposition current value acquired when said second electrochemical cell of said gas sensor in a normal state is in said third state is used as said moisture-related value. Thereby, the measurement control portion can specify the reference water decomposition current value from the acquired second oxygen decomposition current value based on the first correspondence relation.

However, when the output characteristics of the gas sensor is already in an abnormal state, the acquired second oxygen decomposition current value may be inaccurate, and the reference water decomposition current value specified as a result may be inaccurate. It may be difficult to perform an accurate abnormality diagnosis of the output characteristics of the gas sensor in accordance with an abnormality judgment based on such an inaccurate reference water decomposition current value.

Then, when the reference water decomposition current value is specified from the second oxygen decomposition current value as mentioned above, it may be desirable to diagnose whether the output characteristics of the gas sensor is in an abnormal state using some sort of an index, and to correct the reference water decomposition current value specified as mentioned above, according to the change in the output characteristics of the gas sensor from that in a normal state, when judged that the output characteristics of the gas sensor is in an abnormal state.

As the above-mentioned "index", for example, the value of a current which flows between the third electrode and the fourth electrode due to the decomposition of oxygen contained in the test gas when fuel is not supplied to the internal combustion engine can be used. In other words, using the same technique as the above-mentioned FC diagnosis, the change in the output characteristics of the gas sensor from that in a normal state can be detected, and the reference water decomposition current value can be corrected according to this change.

In the above-mentioned case, said measurement control portion may need to have previously memorized a second reference atmosphere decomposition current value which is a value of a current flowing between said third electrode and said fourth electrode due to the decomposition of oxygen contained in said test gas when fuel is not supplied to said internal combustion engine and said second electrochemical cell of said gas sensor in a normal state is in said third state.

The second reference atmosphere decomposition current value can be acquired by measuring a value of a current which flows between the third electrode and the fourth electrode due to the decomposition of oxygen contained in the test gas when fuel is not supplied to the internal combustion engine, in the second electrochemical cell of the gas sensor in a normal state, for example. In addition, the acquired second reference atmosphere decomposition current value can be stored in a data storage device (for instance, ROM, etc.) which an ECU comprises, and can be referred to by a CPU in an abnormality diagnosis of output characteristics of the gas sensor, for example.

Furthermore, said measurement control portion may be configured to acquire the second atmosphere decomposition current value which is a value of a current flowing between said third electrode and said fourth electrode due to the decomposition of oxygen contained in said test gas, based on said second oxygen decomposition current value acquired in said third state when fuel is not supplied to said internal combustion engine. When the gas sensor is in a normal state, the second atmosphere decomposition current value thus acquired and the previously memorized second reference atmosphere decomposition current value may need to be identical. On the other hand, when the output characteristics of the gas sensor is in an abnormal state, the second atmosphere decomposition current value deviates from the second reference atmosphere decomposition current value, according to the change in the output characteristics of the gas sensor from that in a normal state.

Then, said measurement control portion may be configured to correct said specified reference water decomposition current value based on a ratio of said acquired second atmosphere decomposition current value to said second reference atmosphere decomposition current value. Thereby, even if the output characteristics of the gas sensor is already in an abnormal state when the reference water decomposition current value is specified based on the first correspondence relation from the second oxygen decomposition current value acquired as mentioned above, the reference water decomposition current value can be corrected based on the second atmosphere decomposition current value acquired separately. As a result, even if the output characteristics of the gas sensor is already in an abnormal state, the abnormality diagnosis of the output characteristics of the gas sensor can be performed accurately.

However, in order to acquire the above-mentioned second atmosphere decomposition current value, an execution of a fuel cut (FC) may be required like an abnormality diagnosis according to the above-mentioned conventional technology. Therefore, in this case, problems such as the above-mentioned (a) to (c) cannot be eliminated. However, also in this case, based on the decomposition current of water whose decomposition starts in an applied voltage higher than that for oxygen, the existence of an abnormality of the output characteristics of the gas sensor is diagnosed. Therefore, also in this case, an abnormality of the output characteristics of the gas sensor can be diagnosed accurately.

In the above-mentioned case, the measurement control portion can correct the specified reference water decomposition current value based on the ratio of the second atmosphere decomposition current value to the second reference atmosphere decomposition current value acquired by the same technique as the above-mentioned FC diagnosis. However, when the change in the output characteristics of the gas sensor from that in a normal state is excessive and the second atmosphere decomposition current value has remarkably deviated from the second reference atmosphere decomposition current value, the output characteristics of the gas sensor may be abnormal, without correcting the reference water decomposition current value as mentioned above in order to more strictly detect the existence of an abnormality of the output characteristics of the gas sensor based on the second atmosphere decomposition current value.

Then, said measurement control portion may be configured to judge that said gas sensor is abnormal, when a second atmosphere detection deviation, which is a ratio of a value obtained by subtracting said second reference atmosphere decomposition current value from said acquired second atmosphere decomposition current value to said second reference atmosphere decomposition current, is larger than a predetermined third upper limit, or when said second atmosphere detection deviation is smaller than a predetermined third lower limit. In addition, the concrete values of the above-mentioned third upper limit and third lower limit can be suitably defined according to the magnitude of a detection error of the concentration of the test component permitted in the use of the gas sensor to which embodiments of the present disclosure are applied, for example.

In accordance with the above, when the second atmosphere detection deviation deviates from a range determined by the predetermined third upper limit and third lower limit, it can be immediately judged that the output characteristics of the gas sensor is abnormal. Namely, in the above-mentioned case, there may be no need to correct the reference water decomposition current value based on the ratio of the second atmosphere decomposition current value to the second reference atmosphere decomposition current value in order to perform the abnormality diagnosis of the output characteristics of the gas sensor based on the water decomposition current value. Therefore, the existence of an abnormality of the output characteristics of the gas sensor can be judged quickly and simply.

Embodiments of the present disclosure may detect the decomposition current of water ($H_2O$) whose decomposition starts at an applied voltage higher than that for oxygen ($O_2$), in a limited-current type gas sensor which detects oxygen-containing gas contained in an exhaust gas of an internal combustion engine. And, based on the deviation of the decomposition current of water detected as mentioned above from a reference decomposition current of water corresponding to the concentration of water contained in the exhaust gas, the existence of an abnormality of output characteristics of the limited-current type gas sensor can be diagnosed.

Therefore, for example, depending on the material and/or structure, etc., which form the first electrode, even in a case where the gas sensor is not a SOx sensor, sulfur oxide contained in the exhaust gas may be decomposed when water contained in the exhaust gas is also reductively decomposed in the above-mentioned first state. When sulfur oxide is reductively decomposed, its decomposition product may adsorb to the first electrode that is a cathode. As a result, an active surface area of the first electrode may decrease and the magnitude of the electrode current resulting from decomposition of water at the first electrode may fall. In such a case where the first electrode is able to decompose sulfur oxide contained in the test gas in the first state, it may be desirable to reduce the adsorption of the decomposition product of sulfur oxide to the first electrode, at least when the water decomposition current value is acquired in the first state.

Then, said measurement control portion which embodiments of the present disclosure may be configured to raise the temperature of said element portion to a predetermined temperature by using said temperature adjustment portion, in a case where said first electrode can decompose sulfur oxide contained in said test gas in said first state. Thereby, said measurement control portion may prevent the decomposition product of sulfur oxide contained in said test gas from adsorbing to said first electrode.

Specifically, said measurement control portion may maintain the temperature of said element portion at a second predetermined temperature, by using said temperature adjustment portion, when a water decomposition current value is acquired in said first state. The second predetermined temperature may be a temperature not less than said activation temperature and a temperature at which a desorption rate that is a velocity at which a decomposition product of sulfur oxide contained in said test gas desorbs from said first electrode is larger than an adsorption rate that is a velocity at which the decomposition product adsorbs to said first electrode.

The second predetermined temperature as mentioned above can be specified by the following preliminary experiment, for example. First, the first state can be maintained for a predetermined period, and the decomposition product of sulfur oxide made to adsorb to the first electrode. Thereafter, a test gas which contains a sulfur oxide can be supplied to the interior space for a predetermined period, maintaining the temperature of the element portion at various temperatures, and the decrease or increase in the amount of the decomposition product of sulfur oxide adsorbed to the first electrode can be measured. And, a temperature of the element portion at which the amount of the decomposition product adsorbed to the first electrode decreased can be specified as the second predetermined temperature. The decrease or increase in the amount of the decomposition product adsorbed to the first electrode can be measured by a method such as a measurement of the mass of the first electrode and the surface analysis of the first electrode, etc., for example.

In accordance with the above, even though the first electrode may be able to decompose sulfur oxide contained in the test gas in the first state, the measurement control portion may maintain the temperature of the element portion at the second predetermined temperature using the temperature adjustment portion. Thereby, the adsorption of the decomposition product of sulfur oxide contained in the test gas to the first electrode may be reduced. As a result, the active surface area of the first electrode can be maintained and a fluctuation in the magnitude of the electrode current resulting from decomposition of water at the first electrode can also be reduced. Namely, an accurate water decomposition current value can be acquired in the first state. As a result, even though the first electrode is able to decompose sulfur oxide contained in the test gas in the first state, the existence of the abnormality of the output characteristics of the gas sensor can be diagnosed accurately.

Other features of the present disclosure will be understood from the following explanation about embodiments of the present disclosure in reference to the drawings.

DETAILED DESCRIPTION

First Embodiment

Hereafter, an abnormality diagnosis system of a gas sensor according to a first embodiment of the present disclosure (hereafter, referred to as a "first system") will be explained. A gas sensor to which the first system is applied is a one-cell type air-fuel-ratio sensor (oxygen sensor) using a limited-current type oxygen sensor.

Figure 2:
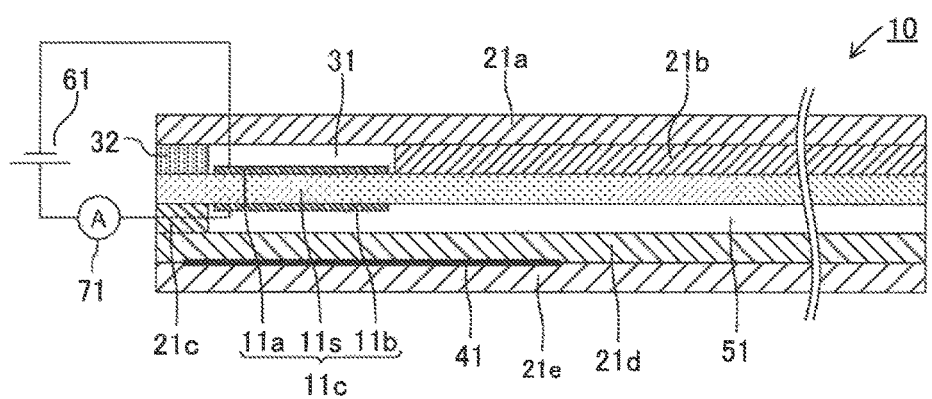
FIG. 2 is a schematic sectional view for showing an example of a configuration of an element portion that a gas sensor to which an abnormality diagnosis system of a gas sensor according to a first embodiment of the present disclosure (first system) is applied comprises.

An element portion 10 of the above-mentioned gas sensor comprises a solid-electrolyte object 11s, a first alumina layer 21a, a second alumina layer 21b, a third alumina layer 21c, a fourth alumina layer 21d, a fifth alumina layer 21e, a diffusion-resistance portion (diffusion-limited layer) 32 and a heater 41, as shown in FIG. 2. The solid-electrolyte object 11s is a thin plate object which comprises zirconia etc. and has oxide ion conductivity. The zirconia which forms the solid-electrolyte object 11s may contain an element, such as scandium (Sc) and yttrium (Y), for example. The first to fifth alumina layers 21a to 21e are compact (gas impermeable) layers (compact objects) which comprises alumina. The diffusion-resistance portion 32 is a porous diffusion-limited layer, and is a gas-permeable layer (thin plate object). The heater 41 is, for example, a thin plate object of the cermet containing platinum (Pt) and ceramics (for instance, an alumina, etc.), and is an exothermic body which generates heat by energization.

Each layer of the element portion 10 is laminated from the lower part in order of the fifth alumina layer 21e, the fourth alumina layer 21d, the third alumina layer 21c, the solid-electrolyte object 11s, the diffusion-resistance portion 32 and the second alumina layer 21b, and the first alumina layer 21a.

An interior space 31 is a space defined by the first alumina layer 21a, the solid-electrolyte object 11s, the diffusion-resistance portion 32 and the second alumina layer 21b, and may be configured so that an exhaust gas of an internal combustion engine as a test gas is introduced into the interior space 31 through the diffusion-resistance portion 32. Namely, in the element portion 10, the interior space 31 is communicated with the inside of an exhaust pipe of the internal combustion engine (neither shown) through the diffusion-resistance portion 32. Therefore, the exhaust gas in the exhaust pipe is introduced into the interior space 31 as the test gas.

A first atmosphere introduction path 51 is defined by the solid-electrolyte object 11s, the third alumina layer 21c and the fourth alumina layer 21d, and is opened to the atmosphere outside of the exhaust pipe. In addition, the first atmosphere introduction path 51 corresponds to the first another space.

The first electrode 11a is a cathode, and the second electrode 11b is an anode. The first electrode 11a is attached to a surface on one side of the solid-electrolyte object 11s (specifically, surface of the solid-electrolyte object 11s, which defines the interior space 31). On the other hand, the second electrode 11b is attached to a surface on the other side of the solid-electrolyte object 11s (specifically, surface of the solid-electrolyte object 11s, which defines the first atmosphere introduction path 51). The first electrode 11a and the second electrode 11b, and the solid-electrolyte object 11s constitute a first electrochemical cell 11c which has oxygen evacuation ability by an oxygen pumping action. This first electrochemical cell $11c$ is heated and is maintained at a desired temperature by the heater 41.

Each layer of the solid-electrolyte object $11s$ and the first to fifth alumina layers $21a$ to $21e$ is formed in the shape of a sheet, for example, by a doctor blade method and an extrusion molding method, etc. The first electrode $11a$ and the second electrode $11b$, and wiring for energizing these electrodes are formed, for example, by a screen printing method, etc. By laminating these sheets as mentioned above and firing them, the element portion 10 which has a structures as mentioned above is integrally manufactured.

The first electrode $11a$ is a porous cermet electrode which contains platinum (Pt) as a principal component. The second electrode $11b$ is also a porous cermet electrode which contains platinum (Pt) as a principal component. However, the material which constitutes the first electrode $11a$ is not limited as long as oxygen (and water) contained in the test gas led to the interior space 31 through the diffusion-resistance portion 32 can be reductively decomposed when a predetermined voltage is applied between the first electrode $11a$ and the second electrode $11b$. The material which constitutes the second electrode $11b$ is not limited to the above, either. The material which constitutes these electrodes can be suitably chosen from various materials widely used as an electrode material of an electrochemical cell using an oxygen pumping action.

The gas sensor further comprises a power supply 61, an ammeter 71 and an ECU that is not shown. The power supply 61 and the ammeter 71 are connected to the ECU. The power supply 61 may be configured to be able to apply a predetermined voltage between the first electrode $11a$ and the second electrode $11b$ so that the electric potential of the second electrode $11b$ is higher than the electric potential of the first electrode $11a$. The operation of the power supply 61 is controlled by the ECU. The ammeter 71 is configured to measure the magnitude of an electrode current which is a current flowing between the first electrode $11a$ and the second electrode $11b$ (i.e., a current which flows through the solid-electrolyte object $11s$) and to output a measured value to the ECU.

As mentioned above, the first electrochemical cell $11c$ and the second electrochemical cell $12c$ are heated by the heater 41. The temperature of the element portion 10 as the result is detected based on the impedance when high frequency voltage is applied between the first electrode $11a$ and the second electrode $11b$. The ECU may be configured to control the power supply to the heater 41 based on the detected temperature, and to control the temperature of the element portion 10. However, the temperature of the element portion 10 may be detected by another temperature sensor which is prepared separately.

The ECU is a microcomputer including a CPU, a ROM which memorizes a program that the CPU performs and a map (data table), etc., and a RAM which temporarily memorizes data (neither is shown). The ECU is connected to actuators (a fuel injection valve, a throttle valve, an EGR valve, etc.) of an internal combustion engine which is not shown. The ECU is configured to transmit a drive (instruction) signal to these actuators and to control the internal combustion engine. The ECU may be programmed to perform the disclosed functions and processes.

The ECU can control the first applied voltage applied between the first electrode $11a$ and the second electrode $11b$. Namely, the power supply 61 and the ECU constitute the voltage-control portion. Specifically, the function of the ECU constituting the voltage-control portion controls an operation of the power supply 61 so that the first applied voltage that is a voltage applied between the first electrode $11a$ and the second electrode $11b$ becomes identical to a target applied voltage. Furthermore, the ECU can receive a signal corresponding to the electrode current which flows through the first electrochemical cell (sensor cell) $11c$ outputted from the ammeter 71. Namely, the ammeter 71 and the ECU constitute the measurement control portion. In addition, the ECU can control the temperature of the element portion 10 by controlling the amount of energization to the heater 41. Namely, the heater 41 and the ECU constitute the temperature adjustment portion. Specifically, the function of the ECU which constitutes any of the measurement control portions outputs a target element temperature, and the function of the ECU which constitutes the temperature adjustment portion controls the amount of energization to the heater 41 based on the target element temperature.

A CPU which the above-mentioned ECU comprises (henceforth, may be simply referred to as a "CPU") heats the element portion 10 to a first predetermined temperature not less than an activation temperature by the heater 41. The activation temperature is a "temperature of the element portion 10" at which the oxide ion conductivity of the solid electrolyte (first solid-electrolyte object $11s$) is expressed. In the present example, the first predetermined temperature is 600° C.

In this state, the CPU applies a voltage (for instance, 0.4 V) corresponding to the limited-current region of oxygen between the first electrode $11a$ and the second electrode $11b$ so that the first electrode $11a$ and the second electrode $11b$ become a cathode and an anode, respectively. Thereby, oxygen contained in the test gas is decomposed at the first electrode $11a$, an oxide ion ($O^{2-}$) is generated, and the generated oxide ion is discharged by an oxygen pumping action from the interior space 31 to the first atmosphere introduction path 51. The magnitude of the electrode current which flows between the first electrode $11a$ and the second electrode $11b$ (first electrode current value) at this time corresponds to the concentration of oxygen contained in the test gas. The ECU receives a signal corresponding to the first electrode current value outputted from the ammeter 71. Thus, the CPU used the first electrochemical cell $11c$ to detect the concentration of oxygen contained in the test gas in the interior space 31. And, based on the detected concentration of oxygen, the air-fuel ratio of the fuel-air mixture supplied to the internal combustion engine is computed.

As mentioned above, in a limited-current type sensor, for example, a crack and jam of a diffusion-resistance portion, a jam of a porous electrode, and a change in the conductivity of a solid electrolyte, etc. may cause an abnormality of output characteristics (for instance, an expansion of a detection value and shrinkage of a detection value, etc.). When the abnormality of output characteristics arises in a limited-current type sensor, it may be difficult to accurately detect the concentration of oxygen contained in an exhaust gas, and it may become difficult to accurately acquire an air-fuel ratio as an air-fuel-ratio sensor.

A diagnostic method in which it is judged that output characteristics of an air-fuel-ratio sensor is abnormal when the output from the sensor is held within the above-mentioned normal range for a predetermined time period or more during the execution of a fuel cut (FC) has been proposed. Such an FC diagnosis will be explained below.

During the execution of the FC (FC execution), since fuel is not supplied to an internal combustion engine and a fuel-air mixture in a combustion chamber is not burned, the aero containing about 21 vol % of oxygen is discharged from the internal combustion engine while maintaining its composition basically. On the other hand, when fuel is supplied to an internal combustion engine and the fuel-air mixture in a combustion chamber is burned, a fuel-air mixture which contains oxygen at a concentration according to the air-fuel ratio of the fuel-air mixture as a result of this burn-up is discharged from the internal combustion engine. For instance, when the air-fuel ratio is maintained near the stoichiometric ratio, oxygen hardly exists in the exhaust gas.

Figure 3:
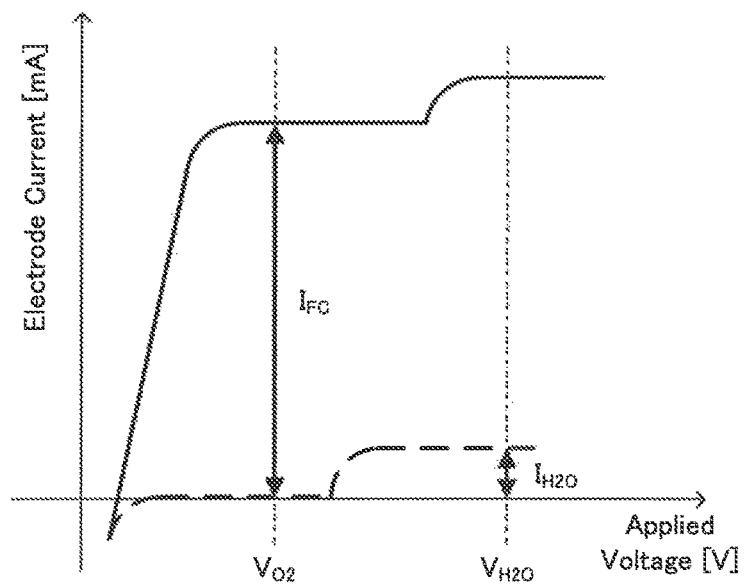
FIG. 3 is a schematic graph for comparing a relation between an applied voltage and an electrode current in a one-cell type air-fuel-ratio sensor in a case where fuel is supplied to an internal combustion engine maintaining an air-fuel ratio near the stoichiometric ratio with that in a case where a fuel cut (FC) is being performed.

Therefore, as shown in FIG. 3, while the magnitude of the electrode current detected during the FC execution at an applied voltage ($V_{O2}$) corresponding to the limited-current region of oxygen (solid line) is very large, the magnitude of the electrode current detected when the air-fuel ratio is maintained in the vicinity of the stoichiometric ratio or less than the vicinity of the stoichiometric ratio (rich) becomes almost 0 (zero) in a case where fuel is supplied to the internal combustion engine (dashed line). On the other hand, since oxygen remains in the exhaust gas when the air-fuel ratio is maintained larger than the stoichiometric ratio (lean), the magnitude of the detected electrode current becomes a value larger than 0 (zero). In the latter case, although a tendency, in which the leaner the air-fuel ratio becomes (the thinner the fuel in the fuel-air mixture is), the larger the magnitude of the electrode current increases, is shown, the magnitude of the above-mentioned electrode current is rather small as compared with the magnitude of the electrode current under the execution of FC ($I_{FC}$). Therefore, when the magnitude of the electrode current at the applied voltage corresponding to the limited-current region of oxygen ($V_{O2}$) is significantly smaller than the above-mentioned $I_{FC}$ even during the execution of FC, it can be judged that the output characteristics of the air-fuel-ratio sensor is abnormal.

However, as mentioned above, by an abnormality diagnostic method of output characteristics of a gas sensor performed based on the magnitude of a decomposition current of oxygen which exists in a comparatively large amount in an exhaust gas as mentioned above, although a large change of the output characteristics can be detected accurately and easily, a minute change of the output characteristics may not be detected accurately and easily.

On the other hand, in the abnormality diagnostic operation of the air-fuel-ratio sensor (oxygen sensor) according to the first system, based on the magnitude of the decomposition current of water, whose decomposition starts at an applied voltage higher than that for oxygen, detected when fuel is supplied to the internal combustion engine, as mentioned above, the existence of an abnormality of the output characteristics of the gas sensor is diagnosed. For instance, when fuel is supplied to the and the internal combustion engine and the air-fuel ratio is maintained in the vicinity of the stoichiometric ratio or less than the vicinity of the stoichiometric ratio (rich), the magnitude of the decomposition current of oxygen becomes almost 0 (zero), as mentioned above. Therefore, in this case, as shown in FIG. 3, it can be said that the magnitude of the electrode current detected at the applied voltage ($V_{H2O}$) at which the reductive decomposition of water occurs is equal to the magnitude of the decomposition current of water (water decomposition current value $I_{H2O}$).

When the air-fuel ratio is maintained larger than the stoichiometric ratio (lean), not only the decomposition current of water, but also the decomposition current of oxygen are included in the detected electrode current since oxygen remains in the exhaust gas. In such a case, for example, a water decomposition current value ($I_{H2O}$) can be computed by subtracting the magnitude of the electrode current detected at the applied voltage which corresponds to the above-mentioned limited-current region of oxygen ($V_{O2}$) (corresponding to the decomposition current value of oxygen ($I_{O2}$)) from the magnitude of the electrode current detected at the applied voltage at which the reductive decomposition of water occurs ($V_{H2O}$) (will be mentioned later in detail).

When the output characteristics of the gas sensor is normal, as a matter of course, the water decomposition current value ($I_{H2O}$) acquired as mentioned above corresponds to the concentration of water contained in the exhaust gas. However, when the output characteristics of the gas sensor is abnormal, the water decomposition current value ($I_{H2O}$) acquired as mentioned above deviates from the normal value of the water decomposition current value corresponding to the concentration of water contained in the exhaust gas (reference water decomposition current value $I_{H2OBASE}$). Therefore, a correspondence relation between the concentration of water contained in the exhaust gas and the reference water decomposition current value ($I_{H2OBASE}$) has been previously prepared for the gas sensor, and based on whether the actually acquired water decomposition current value ($I_{H2O}$) deviates from the reference water decomposition current value corresponding to the concentration of water contained in the exhaust gas at that time ($I_{H2OBASE}$), it can be judged whether the output characteristics of the gas sensor is abnormal or not.

In addition, in air-fuel-ratio sensors (oxygen sensors) with variously changed output characteristics, decomposition current value ($I_{FC}$) of oxygen detected in a FC diagnosis can be measured according to a conventional technology and the water decomposition current value ($I_{H2O}$) detected by the first system, and a correlation between these investigated. In the FC diagnosis according to a conventional technology, an applied voltage corresponding to the limited-current region of oxygen was applied between the electrodes ($V_{O2}$=0.4 V), in a state where fuel was not supplied to the internal combustion engine (FC). In the abnormality diagnosis by the first system, an applied voltage at which the decomposition of water occurred was applied between the electrodes ($V_{H2O}$=1.0 V) while maintaining the air-fuel ratio at the stoichiometric ratio in a state which fuel was supplied to the internal combustion engine (A/F=14.6).

Figure 4:
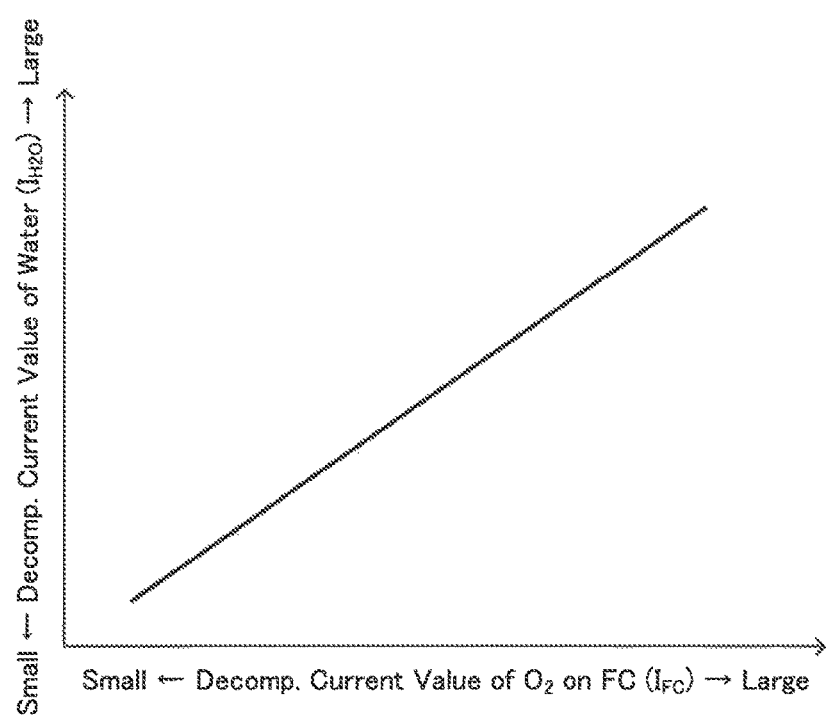
FIG. 4 is a schematic graph for showing a correlation between a decomposition current value ($I_{FC}$) of oxygen detected in a FC diagnosis according to a prior art and a decomposition current value of water ($I_{H2O}$) detected in an abnormality diagnosis according to the present disclosure.

As shown in FIG. 4, the decomposition current value of oxygen ($I_{FC}$) and the water decomposition current value ($I_{H2O}$), which were acquired by the above-mentioned experiment, showed a very good correlation. This shows that the first system which diagnoses an abnormality of output characteristics of a gas sensor based on a water decomposition current value can diagnose the existence of an abnormality of output characteristics of an air-fuel-ratio sensor similarly to a FC diagnosis according to a conventional technology for diagnosing an abnormality of output characteristics of a gas sensor based on the decomposition current value of oxygen.

Figure 5:
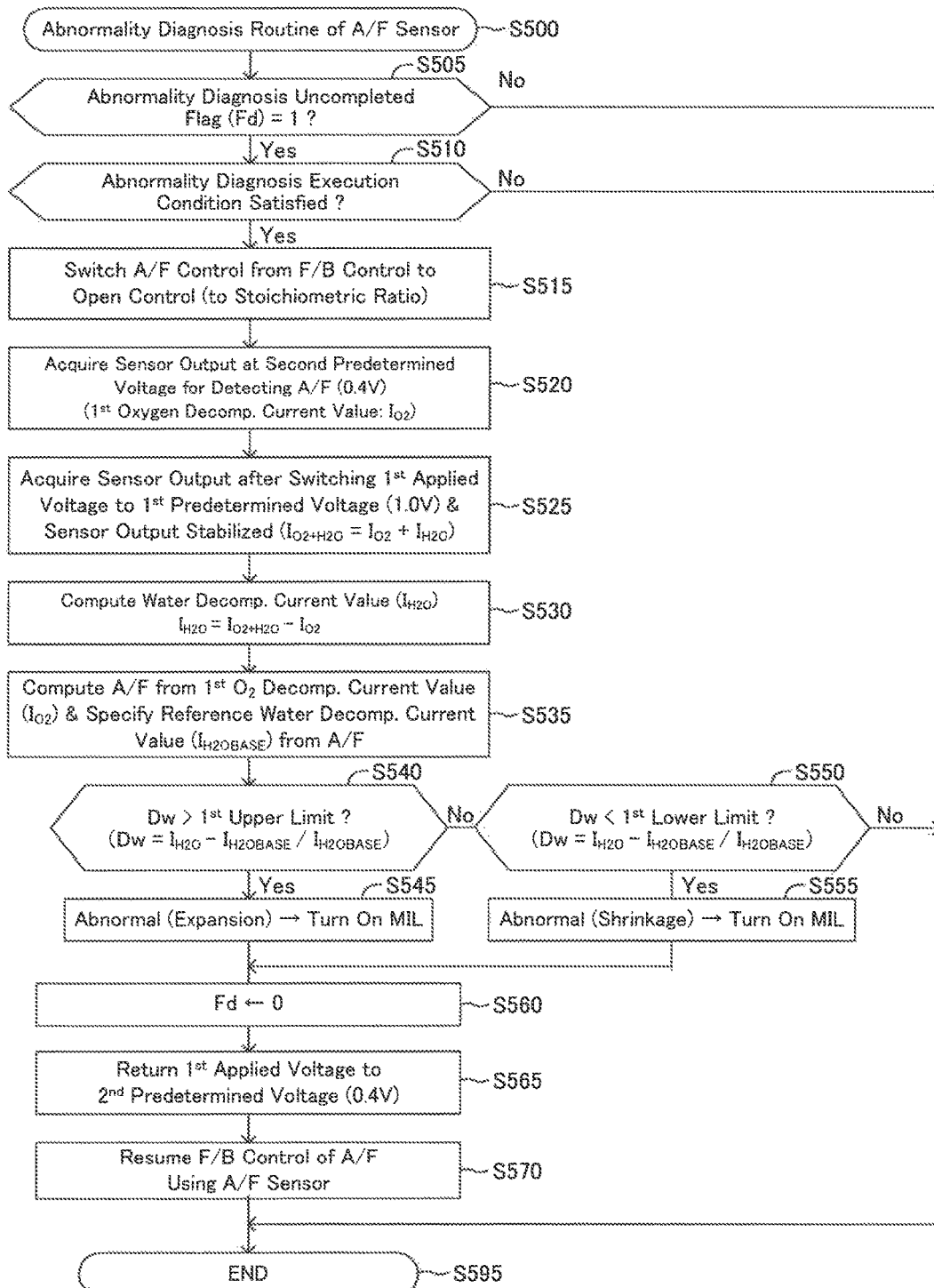
FIG. 5 is a flowchart for showing an example of the abnormality diagnostic operation of a gas sensor, which is performed by the first system.

An abnormality diagnostic operation of a gas sensor (air-fuel-ratio sensor) performed by the first system will be explained more concretely. FIG. 5 is a flowchart for showing an example of an abnormality diagnosis routine of a gas sensor (air-fuel-ratio sensor) performed by the first system. A CPU which the above-mentioned ECU comprises, for instance (henceforth, may be simply referred to as a "CPU") starts treatments from step S500 at a predetermined timing, and progresses to step S505.

In step S505, the CPU judges whether a flag for showing that a diagnosis about whether the output characteristics of the gas sensor is abnormal (henceforth, may be simply referred to as an "abnormality diagnosis") has not yet completed (abnormality diagnosis uncompleted flag: Fd) is raised (is set as "1") or not. This abnormality diagnosis uncompleted flag is set as "1", for example, whenever a certain period has passed or whenever the mileage of a vehicle in which the gas sensor is used increases by a certain distance. On the other hand, as will be mentioned later, this abnormality diagnosis uncompleted flag is set as "0 (zero)" whenever an abnormality diagnosis has been completed.

When judged that the abnormality diagnosis uncompleted flag Fd being set as "1" in the above-mentioned step S505 (S505: Yes), the CPU progresses to the following step S510 and judges whether a condition which should be fulfilled in order to perform the abnormality diagnosis (abnormality diagnosis execution condition) is satisfied. In addition, in the present example, the abnormality diagnosis execution condition is satisfied when all of the following factors (C1) to (C4) are satisfied. However, the abnormality diagnosis execution condition is not limited to the following, and can be suitably defined according to the use of the internal combustion engine to which the gas sensor is applied, etc., for example.

The factors (C1) to (C4) are as follows: (C1) Warm-up of an internal combustion engine to which the gas sensor is applied has been completed. (C2) The above-mentioned internal combustion engine is in an idle state. (C3) A vehicle on which the above-mentioned internal combustion engine is mounted has stopped (speed=0 (zero)). (C4) The temperature of the element portion of the gas sensor is not less than its activation temperature.

When judged that the abnormality diagnosis execution condition being satisfied in the above-mentioned step S510 (S510: Yes), the CPU progresses to the following step S515, suspends the air-fuel-ratio control through a feed-back (F/B) control using the gas sensor (air-fuel-ratio sensor) in the above-mentioned internal combustion engine, and switches to an open control which makes the air-fuel ratio a stoichiometric ratio instead. This is because the air-fuel ratio cannot be detected by the gas sensor since the applied voltage in the gas sensor, etc. are changed into a state which is different from that at a usual time in an abnormality diagnosis, for example.

Next, the CPU progresses to step S520, and acquires the first electrode current value acquired in the second state where the first applied voltage is equal to the second predetermined voltage included in the predetermined second voltage zone, as the test component concentration-related value which is a value associated with the concentration of the test component contained in the test gas. In the present example, since the test component is oxygen, the applied voltage (0.4 V) for detecting oxygen concentration is already the second predetermined voltage (0.4 V). Therefore, the first electrode current value acquired in the second state (namely, test component concentration-related value) is also the first oxygen decomposition current value itself which is a value of a current flowing between the first electrode and the second electrode due to the decomposition of oxygen contained in the test gas. Thus, the CPU acquires the first oxygen decomposition current value ($I_{O2}$).

Next, the CPU progresses to step S525, and switches the first applied voltage to the first predetermined voltage (1.0 V). Namely, the CPU switches the state of the first electrochemical cell 11c from the second state to the first state. And, after a predetermined time period has passed and the output (first electrode current value) of the gas sensor has been stabilized, the sensor output (first electrode current value) is acquired. Since the decomposition starting voltage of oxygen is lower than the decomposition starting voltage of water, not only water, but also oxygen in the test gas are reductively decomposed in the first state. Therefore, this acquired first electrode current value includes not only the electrode current flowing due to the decomposition of water (water decomposition current), but also the electrode current flowing due to the decomposition of oxygen (oxygen decomposition current). On the other hand, since the first predetermined voltage is a voltage included in the decomposition current region of oxygen, the magnitude of this oxygen decomposition current is equal to the first oxygen decomposition current value ($I_{O2}$) acquired in the above-mentioned step S520. Namely, the first electrode current value acquired in step S525 is the sum of the first oxygen decomposition current value ($I_{O2}$) acquired in step S520 and the water decomposition current value ($I_{H2O}$) (the first electrode current value: $I_{O2+H2O}=I_{O2}+I_{H2O}$).

Then, the CPU progresses to the following step S530, and computes the water decomposition current value ($I_{H2O}$) which is the magnitude of the electrode current which flows due to the decomposition of water in the first state, by subtracting the first oxygen decomposition current value ($I_{O2}$) acquired in the above-mentioned step S520 from the first electrode current value ($I_{O2+H2O}$).

In the case where the output characteristics of the gas sensor is normal, the deviation of the water decomposition current value ($I_{H2O}$) computed as mentioned above from the reference water decomposition current value ($I_{H2OBASE}$) which is a value of the water decomposition current corresponding to the concentration of water contained in the test gas at the point in time, which will be detected by the gas sensor with a normal output characteristics, should fall within a predetermined threshold value. On the contrary, when the deviation of the water decomposition current value ($I_{H2O}$) from the reference water decomposition current value ($I_{H2OBASE}$) exceeds the predetermined threshold value, it can be judged that the output characteristics of the gas sensor is abnormal.

Then, the CPU progresses to the following step S535, and specifies the reference water decomposition current value ($I_{H2OBASE}$) at the point in time when the above-mentioned first electrode current value ($I_{O2+H2O}$) is acquired. Specifically, the CPU computes the air-fuel ratio of the corresponding fuel-air mixture from the first oxygen decomposition current value ($I_{O2}$) acquired in the above-mentioned step S520, and specifies the reference water decomposition current value ($I_{H2OBASE}$), from this computed air-fuel ratio, based on a map (data table) which has been memorized previously.

The above-mentioned map is a data table showing a correspondence relation between the air-fuel ratio of the fuel-air mixture supplied to the internal combustion engine and the reference water decomposition current value ($_{IH2OBASE}$) which is the value of a current flowing between the first electrode and the second electrode due to the decomposition of water contained in the test gas when the first electrochemical cell of the gas sensor which has a normal output characteristics is in the first state. Namely, in the present example, the air-fuel ratio of the fuel-air mixture is the moisture-related value, and the correspondence relation between the air-fuel ratio of the fuel-air mixture and the reference water decomposition current value ($I_{H2OBASE}$) is the first correspondence relation.

However, it is not necessarily required to compute the air-fuel ratio of the corresponding fuel-air mixture from the first oxygen decomposition current value ($I_{O2}$) acquired in step S520 as mentioned above. Namely, the first oxygen decomposition current value ($I_{O2}$) may be the moisture-related value, and the correspondence relation between the first oxygen decomposition current value ($I_{O2}$) and the reference water decomposition current value ($I_{H2OBASE}$) may be the first correspondence relation.

Next, the CPU progresses to step S540, and judges whether the moisture detection deviation (Dw) is larger than the predetermined first upper limit. Here, the moisture detection deviation (Dw) is a ratio of a value obtained by subtracting the reference water decomposition current value ($I_{H2OBASE}$) specified from the water decomposition current value ($I_{H2O}$) as mentioned above in step S535 to the reference water decomposition current value ($I_{H2OBASE}$) (Dw= ($I_{H2O}$-$I_{H2OBASE}$)/$I_{H2OBASE}$).

When judged that the moisture detection deviation (Dw) is larger than the predetermined first upper limit in the above-mentioned step S540 (S540: Yes), the gas sensor is in a state where the sensor output is expanded rather than its normal value to be detected excessively (too large) due to the abnormality of the output characteristics. Therefore, the CPU progresses to the following step S545, and makes a judgment that an abnormality of the output characteristics accompanied by an expansion of a detection value have arisen in the gas sensor. The CPU turns on a failure alarm lamp (MIL) corresponding to the judgment, in the present example.

Thereafter, the CPU progresses to the following step S560, and takes down (sets as "0 (zero)") the above-mentioned abnormality diagnosis uncompleted flag Fd. Namely, the CPU records that the abnormality diagnosis about the gas sensor has been completed. Thereafter, the CPU progresses to the following step S565, and returns the first applied voltage to the usual applied voltage (0.4 V) for detecting oxygen concentration. Thereafter, the CPU progresses to the following step S550, resumes the F/B control of the air-fuel ratio using the gas sensor, progresses to step S595, and once ends the routine.

On the other hand, when judged that the moisture detection deviation (Dw) is not larger than the predetermined first upper limit in the above-mentioned step S540 (S540: No), the CPU progresses to step S550, and judges whether the moisture detection deviation (Dw) is smaller than the predetermined first lower limit.

When judged that the moisture detection deviation (Dw) is smaller than the predetermined first upper limit in the above-mentioned step S550 (S550: Yes), the gas sensor is in a state where the sensor output is shrunk rather than its normal value to be detected too small due to the abnormality of the output characteristics. Therefore, the CPU progresses to the following step S555, and makes a judgment that an abnormality of the output characteristics accompanied by shrinkage of a detection value has arisen in the gas sensor. The CPU turns on a failure alarm lamp (MIL) corresponding to the judgment, in the present example.

Thereafter, the CPU progresses to step S560, step S565, step S570 and step S595, and once ends the routine.

In addition, when judged that the abnormality diagnosis uncompleted flag Fd is not set as "1" in the above-mentioned step S505 (S505: No), and, when judged that the abnormality diagnosis execution condition is not satisfied in the above-mentioned step S510 (S510: No), the CPU progresses to step S595 and once ends the routine, without performing any special treatment.

Furthermore, when judged that the moisture detection deviation (Dw) is not smaller than the predetermined first lower limit in the above-mentioned step S550 (S550: No), neither the expansion nor shrinkage of a detection value due to the abnormality of the output characteristics has not occurred in the gas sensor. Therefore, the CPU progresses to step S595 and once ends the routine, without performing any special treatment.

As explained above, in accordance with the first system, in a limited-current type oxygen sensor (air-fuel-ratio sensor) which detects the decomposition current value of oxygen contained in an exhaust gas of an internal combustion engine, the decomposition current value of water ($H_2O$) (water decomposition current) is detected and, based on its deviation from the reference decomposition current value of water (reference water decomposition current) corresponding to the concentration of water contained in the exhaust gas, the existence of an abnormality of output characteristics of the limited-current type gas sensor is diagnosed. Thereby, not only a remarkable abnormality, but also a minute abnormality, of the output characteristics of the gas sensor, can be diagnosed accurately and easily.

In addition, although the gas sensor detected the air-fuel ratio of the fuel-air mixture supplied to the internal combustion engine and the reference water decomposition current value specified from the air-fuel ratio was used as it was in the present example, the reference water decomposition current value may be corrected based on the decomposition current value of oxygen detected at the time of a fuel cut, as mentioned above. Alternatively, as mentioned above, the reference water decomposition current value may be specified from the concentration of water contained in the test gas, which is detected by a separately prepared humidity sensor, etc. Furthermore, for example, the concentration of water contained in a test gas may be estimated based on the temperature of the intake air to the internal combustion engine, and the reference water decomposition current value may be specified from this estimated concentration of water.

Second Embodiment

Hereafter, an abnormality diagnosis system of a gas sensor according to a second embodiment of the present disclosure (hereafter, referred to as a "second system") will be explained. A gas sensor to which the second system is applied is a two-cell type NOx sensor (nitrogen oxide sensor) using a limited-current type oxygen sensor. In the NOx sensor, the second electrochemical cell (pumping cell) on the upstream side decomposes and discharges oxygen in an exhaust gas as a test gas, and the first electrochemical cell (sensor cell) on the downstream side decomposes and detects nitrogen oxide in the test gas.

Figure 6:
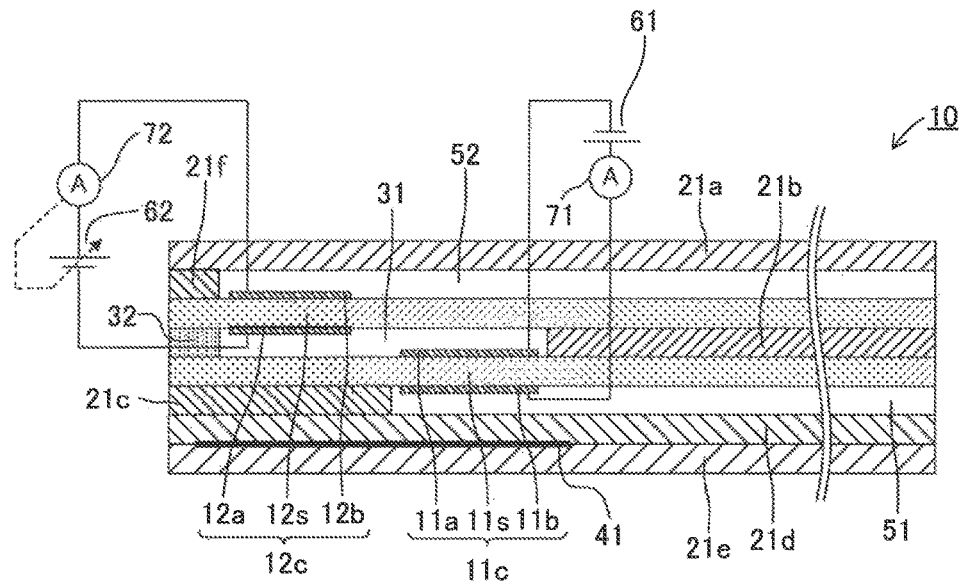
FIG. 6 is a schematic sectional view for showing an example of the configuration of an element portion that a gas sensor, to which an abnormality diagnosis system of a gas sensor according to a second embodiment of the present disclosure (second system) is applied, comprises.

An element portion 10 of the above-mentioned gas sensor comprises a first solid-electrolyte object 11s, a second solid-electrolyte object 12s, a first alumina layer 21a, a second alumina layer 21b, a third alumina layer 21c, a fourth alumina layer 21d, a fifth alumina layer 21e, a sixth alumina layer 21f, a diffusion-resistance portion (diffusion-limited layer) 32 and a heater 41, as shown in FIG. 6.

The solid-electrolyte object 11s is a thin plate object which comprises zirconia etc. and has oxide ion conductivity. The zirconia which forms the solid-electrolyte object 11s may contain an element, such as scandium (Sc) and yttrium (Y), for example. The second solid-electrolyte object 12s is the same as the solid-electrolyte object 11s.

The first to sixth alumina layers 21a to 21f are compact (gas impermeable) layers (compact objects) which comprises alumina. The diffusion-resistance portion 32 is a porous diffusion-limited layer, and is a gas-permeable layer (thin plate object). The heater 41 is, for example, a thin plate object of the cermet containing platinum (Pt) and ceramics (for instance, an alumina, etc.), and is an exothermic body which generates heat by energization.

Each layer of the element portion 10 is laminated from the lower part in order of the fifth alumina layer 21e, the fourth alumina layer 21d, the third alumina layer 21c, the first solid-electrolyte object 11s, the diffusion-resistance portion 32 and the second alumina layer 21b, the second solid-electrolyte object 12s, the sixth alumina layer 21f, and the first alumina layer 21a.

An interior space 31 is a space defined by the first solid-electrolyte object 11s, the second solid-electrolyte object 12s, the diffusion-resistance portion 32 and the second alumina layer 21b, and is configured so that an exhaust gas of an internal combustion engine as a test gas is introduced into the interior space 31 through the diffusion-resistance portion 32. Namely, in the element portion 10, the interior space 31 is communicated with the inside of an exhaust pipe of the internal combustion engine (neither shown) through the diffusion-resistance portion 32. Therefore, the exhaust gas in the exhaust pipe is introduced into the interior space 31 as the test gas.

A first atmosphere introduction path 51 is defined by the first solid-electrolyte object 11s, the third alumina layer 21c and the fourth alumina layer 21d, and is opened to the atmosphere outside of the exhaust pipe. The first atmosphere introduction path 51 corresponds to the first another space. A second atmosphere introduction path 52 is defined by the second solid-electrolyte object 12s, the first alumina layer 21a and the sixth alumina layer 21f, and is opened to the atmosphere outside of the exhaust pipe. The second atmosphere introduction path 52 corresponds to the second another space.

The first electrode 11a is a cathode, and the second electrode 11b is an anode. The first electrode 11a is attached to a surface on one side of the first solid-electrolyte object 11s (specifically, surface of the first solid-electrolyte object 11s, which defines the interior space 31). On the other hand, the second electrode 11b is attached to a surface on the other side of the first solid-electrolyte object 11s (specifically, surface of the first solid-electrolyte object 11s, which defines the first atmosphere introduction path 51). The first electrode 11a and the second electrode 11b are arranged so as to face each other across the first solid-electrolyte object 11s. The first electrode 11a and the second electrode 11b, and the first solid-electrolyte object 11s constitute a first electrochemical cell 11c which has oxygen evacuation ability by an oxygen pumping action.

The third electrode 12a is a cathode, and the fourth electrode 12b is an anode. The third electrode 12a is attached to a surface on one side of the second solid-electrolyte object 12s (specifically, surface of the second solid-electrolyte object 12s, which defines the interior space 31). On the other hand, the fourth electrode 12b is attached to a surface on the other side of the second solid-electrolyte object 12s (for example, surface of the second solid-electrolyte object 12s, which defines the second atmosphere introduction path 52). The third electrode 12a and the fourth electrode 12b are arranged so as to face each other across the second solid-electrolyte object 12s. The third electrode 12a and the fourth electrode 12b, and the second solid-electrolyte object 12s constitute a second electrochemical cell 12c, which has oxygen evacuation ability by an oxygen pumping action. These first electrochemical cell 11c and second electrochemical cell 12c are heated and are maintained at a desired temperature by the heater 41.

Each layer of the first solid-electrolyte object 11s, the second solid-electrolyte object 12s and the first to sixth alumina layers 21a to 21f is formed in the shape of a sheet, for example, by a doctor blade method and an extrusion molding method, etc. The first electrode 11a and the second electrode 11b, the third electrode 12a and the fourth electrode 12b, and wiring for energizing these electrodes are formed, for example, by a screen printing method, etc. By laminating these sheets as mentioned above and firing them, the element portion 10 which has a structures as mentioned above is integrally manufactured.

The first electrode 11a is a porous cermet electrode which contains an alloy of platinum (Pt) and rhodium (Rh) as a principal component, and the second electrode 11b is also a porous cermet electrode which contains platinum (Pt) as a principal component. However, the material which constitutes the first electrode 11a is not limited as long as oxygen and sulfur oxide contained in the test gas led to the interior space 31 through the diffusion-resistance portion 32 can be reductively decomposed when a predetermined voltage is applied between the first electrode 11a and the second electrode 11b. The material which constitutes the first electrode 11a may contain, as a principal component, a platinum group element such as platinum (Pt), rhodium (Rh) and palladium (Pd) or an alloy thereof. The first electrode 11a may be a porous cermet electrode which contains, as a principal component, at least one sort chosen from the group which consists of platinum (Pt), rhodium (Rh) and a palladium (Pd). Furthermore, the material which constitutes the second electrode 11b is not limited to the above, either, and can be suitably chosen from various materials widely used as an anode material of an electrochemical cell using an oxygen pumping action.

On the other hand, the third electrode 12a and the fourth electrode 12b are porous cermet electrodes which contain platinum (Pt) as a principal component. However, the material which constitutes the third electrode 12a is not limited as long as oxygen contained in the test gas led to the interior space 31 through the diffusion-resistance portion 32 can be reductively decomposed when a voltage at which oxygen contained in the test gas can be decomposed (specifically about 0.1 V or more, typically about 0.4 V) is applied between the third electrode 12a and the fourth electrode 12b. Furthermore, the material which constitutes the fourth electrode 12b is not limited to the above, either, and can be suitably chosen from various materials widely used as an anode material of an electrochemical cell using an oxygen pumping action.

In the example shown in FIG. 6, the second electrochemical cell 12c includes the second solid-electrolyte object 12s separate from the first solid-electrolyte object 11s which constitutes the first electrochemical cell 11c. However, the second electrochemical cell 12c may share the first solid-electrolyte object 11s with the first electrochemical cell 11c. In this case, the first atmosphere introduction path 51 functions as the first another space and the second another space.

The gas sensor further comprises a power supply 61, an ammeter 71 and an ECU (Electronic Control Unit) that is not shown. The power supply 61 and the ammeter 71 are connected to the ECU. The power supply 61 is configured to be able to apply a predetermined voltage between the first electrode 11a and the second electrode 11b so that the electric potential of the second electrode 11b is higher than the electric potential of the first electrode 11a. The operation of the power supply 61 is controlled by the ECU. The ammeter 71 is configured to measure the magnitude of an electrode current which is a current flowing between the first electrode 11a and the second electrode 11b (i.e., a current which flows through the first solid-electrolyte object 11s) and to output a measured value to the ECU.

In addition, the gas sensor further comprises a power supply 62 and an ammeter 72. The power supply 62 and the ammeter 72 are connected to the ECU. The power supply 62 is configured to be able to apply a predetermined voltage between the third electrode 12a and the fourth electrode 12b so that the electric potential of the fourth electrode 12b is higher than the electric potential of the third electrode 12a. The operation of the power supply 62 is controlled by the ECU. The ammeter 72 is configured to measure the magnitude of an electrode current which is a current flowing between the third electrode 12a and the fourth electrode 12b (i.e., a current which flows through the second solid-electrolyte object 12s) and to output a measured value to the ECU.

As mentioned above, the first electrochemical cell 11c and the second electrochemical cell 12c are heated by the heater 41. The temperature of the element portion 10 as the result is detected based on the impedance when high frequency voltage is applied between the third electrode 12a and the fourth electrode 12b. The ECU is configured to control the power supply to the heater 41 based on the detected temperature, and to control the temperature of the element portion 10. However, the temperature of the element portion 10 may be detected based on the impedance when high frequency voltage is applied between the first electrode 11a and the second electrode 11b, or, by another temperature sensor which is prepared separately.

The ECU is a microcomputer including a CPU, a ROM which memorizes a program that the CPU performs and a map (data table), etc., and a RAM which temporarily memorizes data (neither is shown). The ECU is connected to actuators (a fuel injection valve, a throttle valve, an EGR valve, etc.) of an internal combustion engine which is not shown. The ECU is configured to transmit a drive (instruction) signal to these actuators and to control the internal combustion engine.

The ECU can control the first applied voltage which is a voltage applied between the first electrode 11a and the second electrode 11b. Namely, the power supply 61 and the ECU constitute the first voltage-control portion. Specifically, the function of the ECU which constitutes the first voltage-control portion controls an operation of the power supply 61 so that the first applied voltage that is a voltage applied between the first electrode 11a and the second electrode 11b becomes identical to a first target applied voltage. Furthermore, the ECU can receive a signal corresponding to the electrode current which flows through the first electrochemical cell 11c outputted from the ammeter 71. Namely, the ammeter 71 and the ECU constitute the first measurement control portion. In addition, the ECU can control a voltage applied between the third electrode 12a and the fourth electrode 12b. Namely, the power supply 62 and the ECU constitute the second voltage-control portion. Specifically, the function of the ECU which constitutes the second voltage-control portion controls an operation of the power supply 71 so that the voltage applied between the third electrode 12a and the fourth electrode 12b becomes identical to a second target applied voltage. Furthermore, the ECU can receive a signal corresponding to the electrode current which flows through the second electrochemical cell 12c outputted from the ammeter 72. Namely, the ammeter 72 and the ECU constitute the second measurement control portion. In addition, the ECU can control the temperature of the element portion 10 by controlling the amount of energization to the heater 41. Namely, the heater 41 and the ECU constitute the temperature adjustment portion. Specifically, the function of the ECU which constitutes any of the measurement control portions outputs a target element temperature, and the function of the ECU which constitutes the temperature adjustment portion controls the amount of energization to the heater 41 based on the target element temperature.

Figure 1:
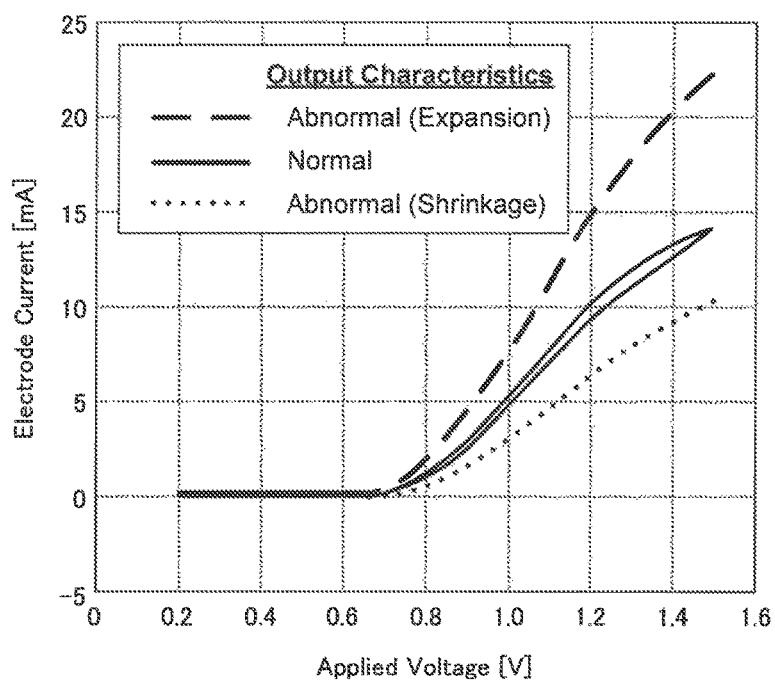
FIG. 1 is a schematic graph for showing a relation of electrode currents detected by an air-fuel-ratio sensor which has a normal output characteristics and an air-fuel-ratio sensor which has an abnormal output characteristics and an applied voltage when the air-fuel ratio of a fuel-air mixture supplied to an internal combustion engine is maintained at the stoichiometric ratio.

In the example shown in FIG. 6, the first and second voltage-control portions are included as separate voltage-control portions. However, these voltage-control portions may be configured as one voltage-control portion, as long as it is possible to apply an expected applied voltage between expected electrodes, respectively. Similarly, in the example shown in FIG. 1, the first and second measurement control portions are included as separate measurement control portions. However, these measurement control portions may be configured as one measurement control portion, as long as it is possible to acquire an expected detection value from between expected electrodes, respectively.

A CPU of the above-mentioned ECU heats the element portion 10 to a first predetermined temperature not less than an activation temperature by the heater 41. The activation temperature is a "temperature of the element portion 10" at which the oxide ion conductivity of the solid electrolyte (first solid-electrolyte object 11s and second solid-electrolyte object 12s) is expressed. In the present example, the first predetermined temperature is 750° C.

In this state, the CPU applies a voltage (for instance, 0.4 V) corresponding to the limited-current region of oxygen between the third electrode 12a and the fourth electrode 12b so that the third electrode 12a and the fourth electrode 12b become a cathode and an anode, respectively. Thereby, oxygen contained in the test gas is decomposed at the third electrode 12a, an oxide ion ($O^2$) is generated, and the generated oxide ion is discharged by an oxygen pumping action from the interior space 31 to the second atmosphere introduction path 52. Thus, the CPU uses the second electrochemical cell 12c to eliminate or substantially eliminate oxygen contained in the test gas in the interior space 31.

The magnitude of the electrode current which flows between the third electrode 12a and the fourth electrode 12b (second oxygen decomposition current value) at this time corresponds to the concentration of oxygen contained in the test gas. The ECU receives a signal corresponding to the second oxygen decomposition current value outputted from the ammeter 71. Thus, the CPU used the second electrochemical cell 12c to detect the concentration of oxygen contained in the test gas in the interior space 31. And, based on the detected concentration of oxygen, the air-fuel ratio of the fuel-air mixture supplied to the internal combustion engine is computed.

On the other hand, the CPU applies a voltage corresponding to the limited-current region of nitrogen oxide ($V_{NOX}$) (for instance, 0.4 V) between the first electrode 11a and the second electrode 11b so that the first electrode 11a and the second electrode 11b become a cathode and an anode, respectively, in a state where the element portion 10 is heated to a first predetermined temperature by the heater 41. As mentioned above, oxygen contained in the test gas in the interior space 31 is substantially eliminated by the second electrochemical cell 12c. Therefore, at the first electrode 11a, nitrogen oxide contained in the test gas is decomposed, and an electrode current accompanying this flows between the first electrode 11a and the second electrode 11b.

Figure 7:
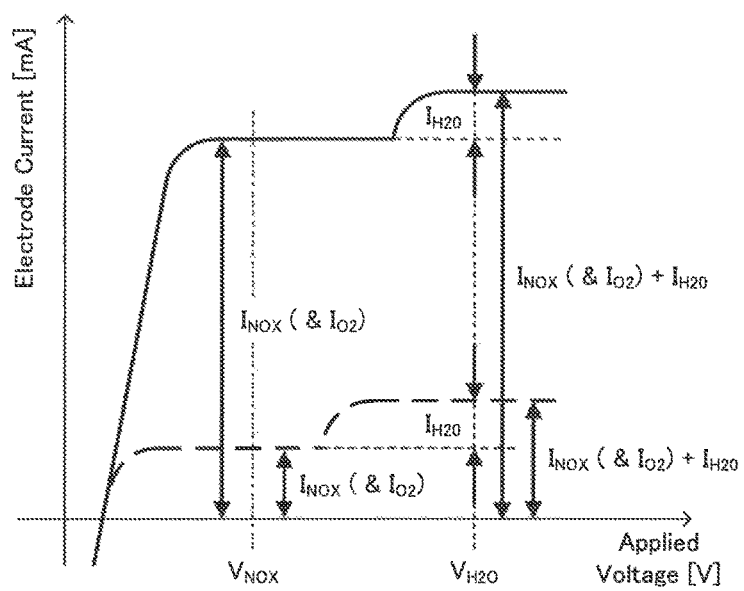
FIG. 7 is a schematic graph for comparing a relation between the first applied voltage and the first electrode current in a two-cell type NOx sensor in a case where the concentration of nitrogen oxide contained in a test gas is high with that in a case where the concentration is low.

As shown in FIG. 7, the magnitude of the above-mentioned electrode current (first electrode current value) is different between a case where the concentration of nitrogen oxide contained in the test gas is high (solid line) and a case where the concentration is low (dashed line). Namely, the first electrode current value varies depending on the concentration of nitrogen oxide contained in the test gas. Thus, the CPU detects the concentration of nitrogen oxide contained in the test gas. In addition, for example, in a case where a pump cell (second electrochemical cell $12c$) is not prepared on the upstream of a sensor cell (the first electrochemical cell $11c$) unlike the NOx sensor in the present example, and in a case where all of oxygen contained in the test gas could not be discharged by the pump cell prepared on the upstream, etc., oxygen exists in the test gas which reaches the sensor cell. In such a case, as shown in the parenthesis in FIG. 7, the first electrode current value includes not only the decomposition current value of nitrogen oxide, but also the decomposition current value of oxygen (limited-current value).

As mentioned above, in an FC diagnosis according to a conventional technology, when the decomposition current value of oxygen ($I_{FC}$) has stayed within a range of the decomposition current value of oxygen detected at the time of an execution of a usual air-fuel-ratio control without performing an FC for a predetermined time period or longer even though a fuel cut (FC) is under execution, it may be judged that the output characteristics of the sensor is abnormal.

However, as mentioned above, by an abnormality diagnostic method of output characteristics of a gas sensor performed based on the magnitude of a decomposition current of oxygen which exists in a comparatively large amount as mentioned above, a minute change of the output characteristics of a NOx sensor which detects the concentration of nitrogen oxide which exists in a slight amount in an exhaust gas may not be detected accurately and easily.

On the other hand, as mentioned above, a second system diagnoses the existence of an abnormality of output characteristics of a NOx sensor, based on the magnitude of the decomposition current of water (water decomposition current value) whose decomposition starts at an applied voltage higher than that for oxygen, detected when fuel is supplied to the internal combustion engine.

The water decomposition current value ($I_{H2O}$) is acquired based on the first electrode current value detected when the first applied voltage is the first predetermined voltage. As shown in the above-mentioned FIG. 7, the first electrode current value detected when the first applied voltage is the first predetermined voltage ($V_{H2O}$) includes the decomposition current value of nitrogen oxide ($I_{NOX}$) and the water decomposition current value ($I_{H2O}$). Therefore, for example, the water decomposition current value ($I_{H2O}$) can be computed by subtracting the magnitude of the first electrode current detected at an applied voltage corresponding to the above-mentioned limited-current region of nitrogen oxide ($V_{NOX}$) (corresponding to the decomposition current of nitrogen oxide ($I_{NOX}$)) from the first electrode current value detected at an applied voltage at which the reductive decomposition of water occurs ($V_{H2O}$) (will be mentioned later in detail).

As mentioned above about the first system, based on whether the water decomposition current value ($I_{H2O}$) thus acquired has deviated from the reference water decomposition current value ($I_{H2OBASE}$) corresponding to the concentration of water contained in the exhaust gas at that time, it can be judged whether the output characteristics of the NOX sensor is abnormal.

Using NOx sensors with variously changed output characteristics, the decomposition current value ($I_{NOX}$) of nitrogen oxide contained in an exhaust gas containing a constant concentration (100 ppm) of nitrogen oxide and the water decomposition current value ($I_{H2O}$) detected by the second system while supplying the fuel-air mixture with a constant air-fuel ratio (A/F=20) to an internal combustion engine was measured, and the correlation between these was investigated. In the first electrochemical cell $11c$, the decomposition current of nitrogen oxide ($I_{NOX}$) is detected at the first applied voltage set as 0.4 V, and the decomposition current of water ($I_{H2O}$) is detected at the first applied voltage set as 1.0 V.

In addition, when an applied voltage at which the reductive decomposition of water occurs is applied between the first electrode $11a$ and the second electrode $11b$ having the above-mentioned configurations, not only water, but also sulfur oxide contained in a test gas are decomposed reductively. As will be mentioned later, depending on the temperature of the element portion 10, the decomposition product of sulfur oxide may adsorb to the first electrode $11a$. However, since the first predetermined temperature in the present example is 750° C., the decomposition product of sulfur oxide does not adsorb to the first electrode $11a$.

Figure 8:
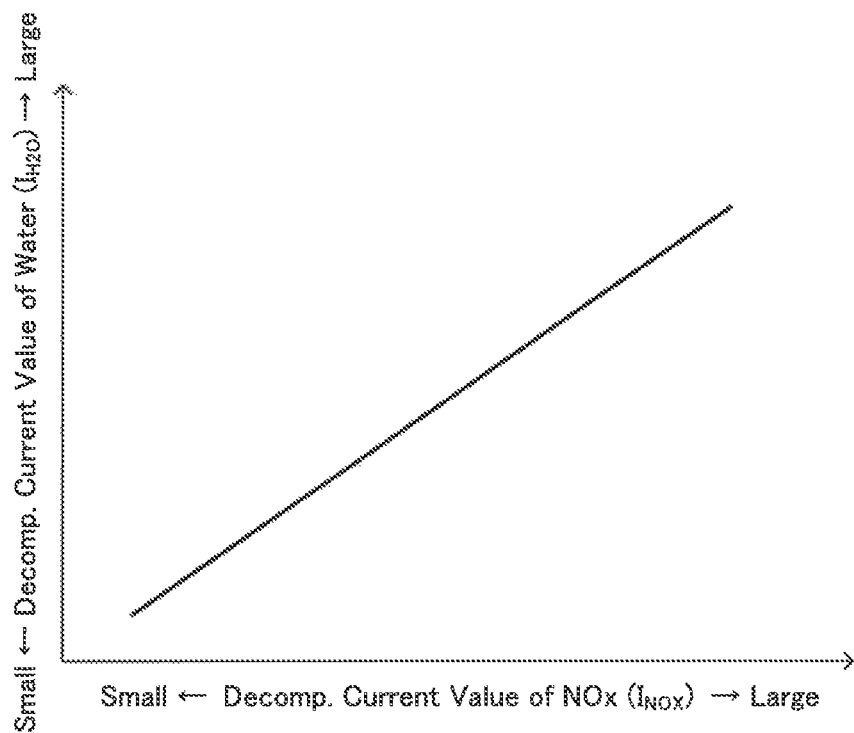
FIG. 8 is a schematic graph for showing a correlation between a decomposition current value of nitrogen oxide ($I_{NOX}$) detected by a NOx sensor and a decomposition current value of water ($I_{H2O}$) detected in the abnormality diagnosis by the second system.

As shown in FIG. 8, the decomposition current value of nitrogen oxide ($I_{NOX}$) and the water decomposition current value ($I_{H2O}$) which were acquired by the above-mentioned experiment showed a very good correlation. This correlation shows that the water decomposition current value ($I_{H2O}$) used for an abnormality diagnosis of a gas sensor by the second system is suitable as an index for diagnosing an abnormality of the output characteristics of the decomposition current value of nitrogen oxide ($I_{NOX}$).

Here, an abnormality diagnostic operation of a gas sensor (NOx sensor) performed by the second system will be explained. In addition, in the present example, the air-fuel ratio of the fuel-air mixture supplied to the internal combustion engine is detected by the gas sensor, and the reference water decomposition current value specified from the air-fuel ratio is not used as it is, and the reference water decomposition current value is corrected based on the decomposition current value of oxygen detected at the time of the execution of a fuel cut (FC), as mentioned above. Furthermore, in the present example, when the decomposition current value of oxygen detected at the time of the FC execution has largely deviated from a reference value, it is judged that the gas sensor is abnormal, and the abnormality diagnosis of the gas sensor based on the water decomposition current value is not performed.

Figure 9:
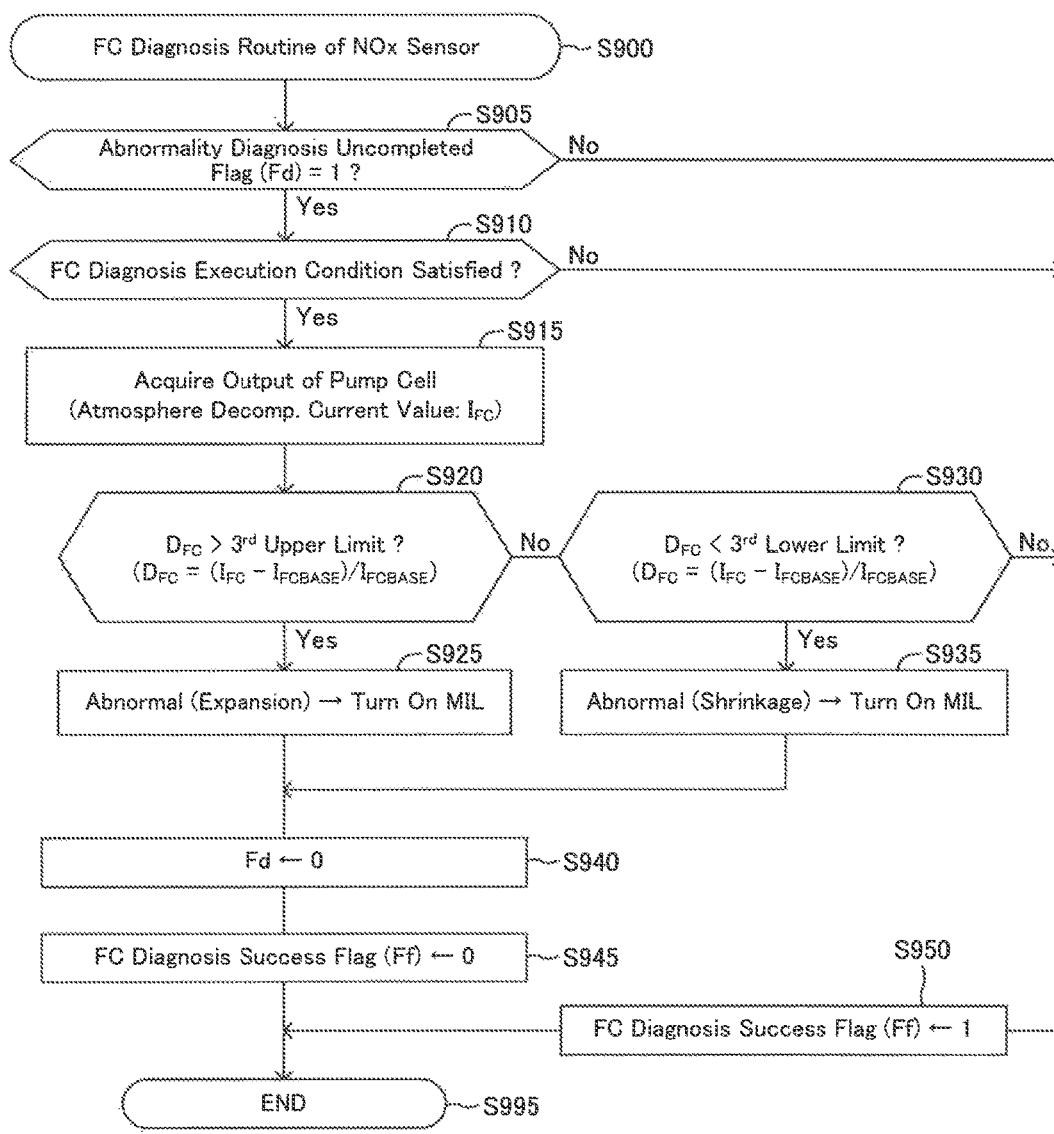
FIG. 9 is a flowchart for showing an example of an FC diagnostic operation of a gas sensor, which is performed by the second system.

Then, the abnormality diagnosis (FC diagnosis) of the gas sensor based on the decomposition current value of oxygen detected at the time of the execution of FC (atmosphere decomposition current value) will be explained first. FIG. 9 is a flowchart for showing an example of an FC diagnostic routine of a gas sensor (NOx sensor) performed by the second system is shown. For instance, the CPU of the above-mentioned ECU (henceforth, may be simply referred to as the "CPU") starts treatments from step S900 at a predetermined timing, and progresses to step S905.

In step S905, the CPU judges whether a flag for showing that a diagnosis about whether the output characteristics of the gas sensor is abnormal (henceforth, may be simply referred to as an "abnormality diagnosis") has not yet completed (abnormality diagnosis uncompleted flag: Fd) is raised (is set as "1") or not. This abnormality diagnosis uncompleted flag is set as "1", for example, whenever a certain period has passed or whenever the mileage of a vehicle in which the gas sensor is used increases by a certain distance. On the other hand, will be mentioned later, this abnormality diagnosis uncompleted flag is set as "0 (zero)" whenever an abnormality diagnosis has been completed.

When judged that the abnormality diagnosis uncompleted flag Fd being set as "1" in the above-mentioned step S905 (S905: Yes), the CPU progresses to the following step S910 and judges whether a condition which should be fulfilled in order to perform the FC diagnosis (FC diagnosis execution condition) is satisfied. In addition, in the present example, the FC diagnosis execution condition is satisfied when all of the following (F1) to (F3) are satisfied. However, the FC diagnosis execution condition is not limited to the following, and can be suitably defined according to the use of the internal combustion engine to which the gas sensor is applied, etc., for example.

The following are factors (F1) to (F3): (F1) Warm-up of an internal combustion engine to which the gas sensor is applied has been completed. (F2) A predetermined time period has passed since the execution of a fuel cut (FC) was started. (F3) The temperature of the element portion of the gas sensor is not less than its activation temperature.

When judged that the FC diagnosis execution condition being satisfied in the above-mentioned step S910 (S910: Yes), the CPU progresses to the following step S915, and acquires the second atmosphere decomposition current value ($I_{FC}$) which is the value of a current which flows between the third electrode 12a and the fourth electrode 12b due to the decomposition of oxygen contained in the test gas, from the second electrochemical cell 12c (pump cell) in the third state.

Next, the CPU progresses to step S920, and reads the second reference atmosphere decomposition current value ($I_{FCBASE}$) previously stored in the data storage device (for instance, ROM, etc.) which the ECU comprises. The second reference atmosphere decomposition current value ($I_{FCBASE}$) is the value of the current which flows between the third electrode 12a and the fourth electrode 12b due to the decomposition of oxygen contained in the test gas when the second electrochemical cell 12c of the gas sensor in a normal state is in the third state during the FC execution, as mentioned above. And, the CPU computes the second atmosphere detection deviation ($D_{FC}$) which is a ratio of a value obtained by subtracting the second reference atmosphere decomposition current value ($I_{FCBASE}$) from the second atmosphere decomposition current value ($I_{FC}$) acquired in step S915 to the second reference atmosphere decomposition current value ($I_{FCBASE}$).

When the output characteristics of the gas sensor is normal, the deviation of the second atmosphere decomposition current value ($I_{FC}$) acquired as mentioned above from the second reference atmosphere decomposition current value ($I_{FCBASE}$) should fall within a predetermined threshold value. On the contrary, when the deviation of the second atmosphere decomposition current value ($I_{FC}$) from the second reference atmosphere decomposition current value ($I_{FCBASE}$) exceeds the predetermined threshold value, it can be judged that the output characteristics of the gas sensor is abnormal. Therefore, the CPU judges whether the above-mentioned second atmosphere detection deviation ($D_{FC}$) is larger than a predetermined third upper limit in step S920.

When judged that the second atmosphere detection deviation ($D_{FC}$) is larger than the predetermined third upper limit in the above-mentioned step S920 (S920: Yes), the gas sensor is in a state where the sensor output is expanded rather than its normal value to be detected excessively (too large) due to the abnormality of the output characteristics. Therefore, the CPU progresses to the following step S925, and make a judgment that an abnormality of the output characteristics accompanied by an expansion of a detection value has arisen in the gas sensor. The CPU turns on a failure alarm lamp (MIL) corresponding to the judgment, in the present example.

Thereafter, the CPU progresses to the following step S940, and takes down (sets as "0 (zero)") the above-mentioned abnormality diagnosis uncompleted flag Fd. Namely, the CPU records that the abnormality diagnosis about the gas sensor has been completed. Thereafter, the CPU progresses to the following step S945, and takes down (sets as "0 (zero)") an FC diagnosis success flag (Ff) for showing that the output characteristics of the gas sensor has been judged to be normal by the FC diagnosis. Thereafter, the CPU progresses to the following step S995, and once ends the routine.

On the other hand, when judged that the second atmosphere detection deviation ($D_{FC}$) is not larger than the predetermined third upper limit in the above-mentioned step S920 (S920: No), the CPU progresses to step S930, and judges whether the second atmosphere detection deviation ($D_{FC}$) is smaller than a predetermined third lower limit.

When judged that the second atmosphere detection deviation (DFC) is smaller than the predetermined third lower limit in the above-mentioned step S930 (S930: Yes), the gas sensor is in a state where the sensor output is shrunk rather than its normal value to be detected too small due to the abnormality of the output characteristics. Therefore, the CPU progress to the following step S935, and makes a judgment that an abnormality of the output characteristics accompanied by shrinkage of a detection value has arisen in the gas sensor. The CPU turns on a failure alarm lamp (MIL) corresponding to the judgment, in the present example.

Thereafter, the CPU progresses to step S940, step S945 and step S995, and once ends the routine.

In addition, when judged that the abnormality diagnosis uncompleted flag Fd is not set as "1" in the above-mentioned step S905 (S905: No), and, when judged that the FC diagnosis execution condition is not satisfied in the above-mentioned step S910 (S910: No), the CPU progresses to step S995 and once ends the routine, without performing any special treatment.

Furthermore, when judged that the second atmosphere detection deviation ($D_{FC}$) is not smaller than the predetermined third lower limit in the above-mentioned step S930 (S930: No), neither the expansion nor shrinkage of a detection value due to the abnormality of the output characteristics has not occurred in the gas sensor. Therefore, the CPU progresses to step S950, and raises the FC diagnosis success flag (Ff) (sets as "1"). Thereafter, the CPU progresses to the following step S995, and once ends the routine.

As explained above, in accordance with the second system, it is judged whether output characteristics of the gas sensor is abnormal or not, based on the decomposition current of oxygen detected during the FC execution. Thereby, when judged that the output characteristics of the gas sensor is abnormal, there is no need to correct the reference water decomposition current value based on the ratio of the second atmosphere decomposition current value to the second reference atmosphere decomposition current value in order to perform the abnormality diagnosis of the output characteristics of the gas sensor based on the water decomposition current value as will be mentioned later. Therefore, the existence of an abnormality of the output characteristics of the gas sensor can be judged quickly and simply.

Figure 10:
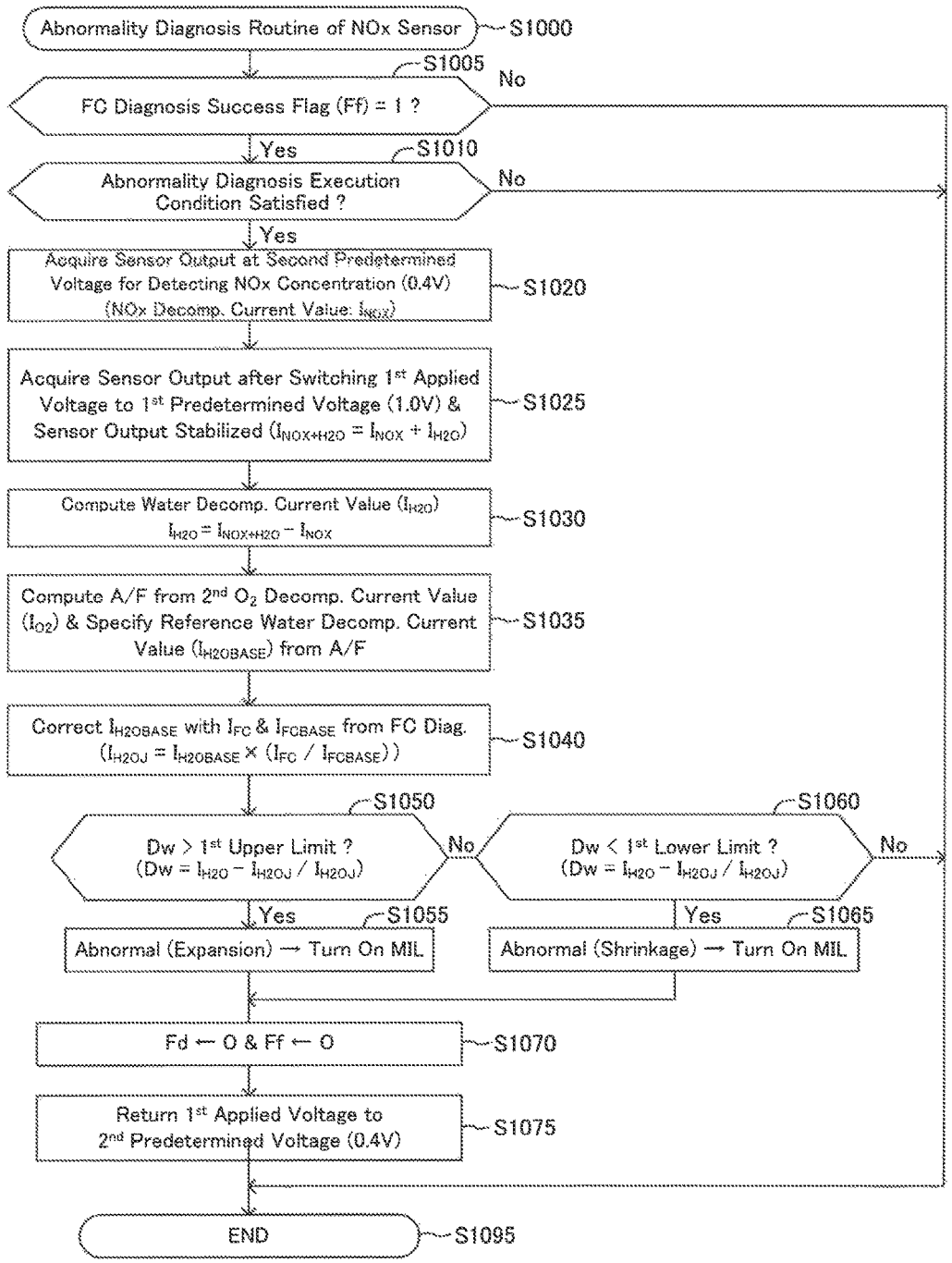
FIG. 10 is a flowchart for showing an example of an abnormality diagnostic operation of a gas sensor, which is performed by the second system.

Next, the abnormality diagnosis of the gas sensor based on the water decomposition current value performed by the second system will be explained. FIG. 10 is a flowchart for showing an example of the abnormality diagnosis routine of the gas sensor (NOx sensor) performed by the second system. For instance, the CPU of the above-mentioned ECU starts treatments from step S1000 at a predetermined timing, and progresses to step S1005.

In step S1005, the CPU judges whether the FC diagnosis success flag (Ff) for showing that the output characteristics of the gas sensor has been judged to be normal by the above-mentioned FC diagnosis has been raised or not (whether it has been set as "1" or not). This FC diagnosis success flag Ff is raised (set as "1") when judged that the output characteristics of the gas sensor being normal by the FC diagnosis as mentioned above. On the other hand, it is taken down (set as "0 (zero)"), when judged that the output characteristics of the gas sensor is abnormal by the FC diagnosis, and when the abnormality diagnosis, which will be explained from now on, has been completed.

When judged that the FC diagnosis success flag Ff has been set as "1" in the above-mentioned step S1005 (S1005: Yes), the CPU progress to the following step S1010, and judges whether a condition which should be fulfilled in order to perform the abnormality diagnosis (abnormality diagnosis execution condition) is satisfied. In addition, in the present example, the abnormality diagnosis execution condition is satisfied when all of the (C1) to (C4), which were mentioned above about the first system, are satisfied. However, the abnormality diagnosis execution condition is not limited to the above, and can be suitably defined according to the use of the internal combustion engine to which the gas sensor is applied, etc., for example.

When judged that the abnormality diagnosis execution condition is satisfied in the above-mentioned step S1010 (S1010: Yes), the CPU progresses to the following step S1020, and acquires the first electrode current value acquired in the second state where the first applied voltage is equal to the second predetermined voltage included in the predetermined second voltage zone, as the test component concentration-related value which is a value associated with the concentration of the test component contained in the test gas. In the present example, since the test component is nitrogen oxide, the second predetermined voltage (0.4 V) is set to a voltage (0.4 V) corresponding to the limited-current region of nitrogen oxide.

Furthermore, as mentioned above, in the present example, oxygen contained in the test gas introduced into the interior space 31 of the element portion 10 is decomposed by the second electrochemical cell 12c as a pump cell disposed on the upstream side of the first electrochemical cell 11c as a sensor cell, and is discharged from the interior space. As a result, the concentration of oxygen contained in the test gas which has arrived at the first electrode 11a that is a cathode of the first electrochemical cell 11c is substantially 0 (zero), or is extremely low.

Therefore, the first electrode current value acquired in the second state (namely, test component concentration-related value) is the NOx decomposition current value itself which is the value of the current flowing between the first electrode and the second electrode due to the decomposition of nitrogen oxide contained in the test gas. Thus, the CPU acquires the NOx decomposition current value ($I_{NOX}$).

Next, the CPU progresses to step S1025, and switches the first applied voltage to the first predetermined voltage (1.0 V). Namely, the CPU switches the state of the first electrochemical cell 11c from the second state to the first state. And, after a predetermined time period has passed and the output (first electrode current value) of the gas sensor has been stabilized, the sensor output (first electrode current value) is acquired. Since the decomposition starting voltage of nitrogen oxide is lower than the decomposition starting voltage of water, not only water, but also nitrogen oxide in the test gas are reductively decomposed in the first state. Therefore, this acquired first electrode current value includes not only the electrode current flowing due to the decomposition of water (water decomposition current), but also the electrode current flowing due to the decomposition of nitrogen oxide (NOx decomposition current). On the other hand, since the first predetermined voltage is a voltage included in the decomposition current region of nitrogen oxide, the magnitude of this NOx decomposition current is equal to the NOx decomposition current value ($I_{NOX}$) acquired in the above-mentioned step S1020. Namely, the first electrode current value acquired in step S1025 is the sum of the NOx decomposition current value ($I_{NOX}$) acquired in step S1020 and the water decomposition current value ($I_{H2O}$) (the first electrode current value: $I_{NOX+H2O}=I_{NOX}+I_{H2O}$).

Then, the CPU progresses to the following step S1030, and computes the water decomposition current value ($I_{H2O}$) which is the magnitude of the electrode current which flows due to the decomposition of water in the first state, by subtracting the NOx decomposition current value ($I_{NOX}$) acquired in the above-mentioned step S1020 from the first electrode current value ($I_{NOX+H2O}$).

In the case where the output characteristics of the gas sensor is normal, the deviation of the water decomposition current value ($I_{H2O}$) computed as mentioned above from the reference water decomposition current value ($I_{H2OBASE}$) which is a value of the water decomposition current corresponding to the concentration of water contained in the test gas at the point in time, which will be detected by the gas sensor with a normal output characteristics, should fall within a predetermined threshold value. On the contrary, when the deviation of the water decomposition current value ($I_{H2O}$) from the reference water decomposition current value ($I_{H2OBASE}$) exceeds the predetermined threshold value, it can be judged that the output characteristics of the gas sensor is abnormal.

Then, the CPU progresses to the following step S1035, and specifies the reference water decomposition current value ($I_{H2OBASE}$) at the point in time when the above-mentioned first electrode current value ($I_{NOX+H2O}$) is acquired. Specifically, the CPU computes the air-fuel ratio of the corresponding fuel-air mixture from the second oxygen decomposition current value ($I_{O2}$) acquired separately in the second electrochemical cell 12c that is a pump cell, and specifies the reference water decomposition current value ($I_{H2OBASE}$), from this computed air-fuel ratio, based on a map (data table) which may have been memorized previously.

The above-mentioned map is a data table showing a correspondence relation between the air-fuel ratio of the fuel-air mixture supplied to the internal combustion engine and the reference water decomposition current value ($I_{H2OBASE}$) which is the value of a current flowing between the third electrode and the fourth electrode due to the decomposition of water contained in the test gas when the second electrochemical cell of the gas sensor which has a normal output characteristics is in the third state. Namely, in the present example, the air-fuel ratio of the fuel-air mixture is the moisture-related value, and the correspondence relation between the air-fuel ratio of the fuel-air mixture and the reference water decomposition current value ($I_{H2OBASE}$) is the first correspondence relation.

However, it is not necessarily required to compute the air-fuel ratio of the corresponding fuel-air mixture from the second oxygen decomposition current value ($I_{O2}$) acquired separately in a pump cell. Namely, the second oxygen decomposition current value ($I_{O2}$) may be the moisture-related value, and the correspondence relation between the second oxygen decomposition current value ($I_{O2}$) and the reference water decomposition current value ($I_{H2OBASE}$) may be the first correspondence relation.

Next, the CPU progresses to step S1040, and correct the reference water decomposition current value ($I_{H2OBASE}$) specified in the above-mentioned step S1035, based on the second atmosphere decomposition current value ($I_{FC}$) and second reference atmosphere decomposition current value ($I_{FCBASE}$) which were acquired in the above-mentioned FC diagnosis. Specifically, the CPU computes a corrected reference water decomposition current value ($I_{H2OJ}$) by multiplying the reference water decomposition current value ($I_{H2OBASE}$) by a ratio of the second atmosphere decomposition current value ($I_{FC}$) to the second reference atmosphere decomposition current value ($I_{FCBASE}$).

Next, the CPU progresses to step S1050, and judges whether the moisture detection deviation (Dw) is larger than the predetermined first upper limit. Here, the moisture detection deviation (Dw) is a ratio of a value obtained by subtracting the reference water decomposition current value ($I_{H2OJ}$) corrected in step S1040 as mentioned above from the water decomposition current value ($I_{H2O}$) to the reference water decomposition current value ($I_{H2OJ}$) (Dw=($I_{H2O}$−$I_{H2OJ}$)/$I_{H2OJ}$).

When judged that the moisture detection deviation (Dw) is larger than the predetermined first upper limit in the above-mentioned step S1050 (S1050: Yes), the gas sensor is in a state where the sensor output is expanded rather than its normal value to be detected excessively (too large) due to the abnormality of the output characteristics. Therefore, the CPU progresses to the following step S1055, and makes a judgment that an abnormality of the output characteristics accompanied by an expansion of a detection value have arisen in the gas sensor. The CPU turns on a failure alarm lamp (MIL) corresponding to the judgment, in the present example.

Thereafter, the CPU progresses to the following step S1070, and takes down (sets as "0 (zero)") both the above-mentioned abnormality diagnosis uncompleted flag Fd and the FC diagnosis success flag Ff. Namely, the CPU records that the abnormality diagnosis about the gas sensor has been completed, and resets the FC diagnosis. Thereafter, the CPU progresses to the following step S1075, and returns the first applied voltage to the second predetermined voltage (0.4 V). Thereafter, the CPU progresses to the following step S1095, and once ends the routine.

On the other hand, when judged that the moisture detection deviation (Dw) is not larger than the predetermined first upper limit in the above-mentioned step S1050 (S1050: No), the CPU progresses to step S1060, and judges whether the moisture detection deviation (Dw) is smaller than the predetermined first lower limit.

When judged that the moisture detection deviation (Dw) is smaller than the predetermined first upper limit in the above-mentioned step S1060 (S1060: Yes), the gas sensor is in a state where the sensor output is shrunk rather than its normal value to be detected too small due to the abnormality of the output characteristics. Therefore, the CPU progresses to the following step S1065, and makes a judgment that an abnormality of the output characteristics accompanied by shrinkage of a detection value has arisen in the gas sensor.

The CPU turns on a failure alarm lamp (MIL) corresponding to the judgment, in the present example.

Thereafter, the CPU progresses to step S1070, step S1075 and step S1095, and once ends the routine.

In addition, when judged that the FC diagnosis success flag Ff is not set as "1" in the above-mentioned step S1005 (S1005: No), and, when judged that the abnormality diagnosis execution condition is not satisfied in the above-mentioned step S1010 (S1010: No), the CPU progresses to step S1095 and once ends the routine, without performing any special treatment.

Furthermore, when judged that the moisture detection deviation (Dw) is not smaller than the predetermined first lower limit in the above-mentioned step S1060 (S1060: No), neither the expansion nor shrinkage of a detection value due to the abnormality of the output characteristics has not occurred in the gas sensor. Therefore, the CPU progresses to step S1095 and once ends the routine, without performing any special treatment.

As explained above, in accordance with the second system, in a limited-current type oxygen sensor (NOx sensor) which detects the decomposition current value of nitrogen oxide contained in an exhaust gas of an internal combustion engine, the decomposition current value of water ($H_2O$) (water decomposition current) is detected and, based on its deviation from the reference decomposition current value of water (reference water decomposition current) corresponding to the concentration of water contained in the exhaust gas, the existence of an abnormality of output characteristics of the limited-current type gas sensor is diagnosed. Thereby, not only a remarkable abnormality, but also a minute abnormality, of the output characteristics of the gas sensor, can be diagnosed accurately and easily.

In addition, although the air-fuel ratio of the fuel-air mixture supplied to an internal combustion engine is detected by the gas sensor, and the reference water decomposition current value specified from the air-fuel ratio is corrected based on the decomposition current value of oxygen, which is detected at the time of the fuel cut, in the present example, the reference water decomposition current value may be used as it is, without correcting the reference water decomposition current value. Alternatively, as mentioned above, the reference water decomposition current value may be specified from the concentration of water contained in the test gas, which is detected by a separately prepared humidity sensor, etc. Furthermore, for example, the concentration of water contained in the test gas may be estimated based on the temperature of the intake air to the internal combustion engine, and the reference water decomposition current value may be specified from this estimated concentration of water. In addition, when judged that the output characteristics of the gas sensor is normal, the second reference atmosphere decomposition current value ($I_{FCBASE}$) may be updated (learned) with the second atmosphere decomposition current value ($I_{FC}$) acquired in the above-mentioned FC diagnosis.

In the present example, the water decomposition current value ($I_{H2O}$) which is the magnitude of the electrode current which flows due to the decomposition of water in the first state was computed by subtracting the NOx decomposition current value ($I_{NOX}$) acquired in the above-mentioned step S1020 from the first electrode current value ($I_{NOX+H2O}$). However, the concentration of nitrogen oxide contained in a test gas (ppm order) is sufficiently small as compared with the concentration of water contained in the test gas (% order). Therefore, the first electrode current value ($I_{NOx+H2O}$) may be used as the water decomposition current value ($I_{H2O}$) as it is.

Hereafter, an abnormality diagnosis system of a gas sensor according to the third embodiment of the present disclosure (hereafter, referred to as a "third system") will be explained. A gas sensor to which the third system is applied is a two-cell type SOx sensor (sulfur oxide sensor) using a limited-current type oxygen sensor. In the SOx sensor, the second electrochemical cell (pumping cell) on the upstream side decomposes and discharges oxygen in an exhaust gas as a test gas, and the first electrochemical cell (sensor cell) on the downstream side decomposes and detects sulfur oxide in the test gas. In addition, the SOx sensor shown in the present example detects the concentration of the sulfur oxide based on a phenomenon in which the magnitude of the decomposition current of water in the first electrochemical cell (sensor cell) on the downstream side changes according to the concentration of sulfur oxide contained in a test gas.

Since the element portion 10 of the above-mentioned gas sensor has the same configuration as the element portion 10 of the gas sensor to which the second system is applied, which has been explained referring to FIG. 6, no explanation about it will be repeated here.

A CPU of the above-mentioned ECU heats the element portion 10 to a first predetermined temperature not less than an activation temperature by the heater 41. The activation temperature is a "temperature of the element portion 10" at which the oxide ion conductivity of the solid electrolyte (first solid-electrolyte object 11s and second solid-electrolyte object 12s) is expressed. In the present example, the first predetermined temperature is 600° C.

In this state, the CPU applies a voltage (for instance, 0.4 V) corresponding to the limited-current region of oxygen between the third electrode 12a and the fourth electrode 12b so that the third electrode 12a and the fourth electrode 12b become a cathode and an anode, respectively. Thereby, oxygen contained in the test gas is decomposed at the third electrode 12a, an oxide ion ($O^{2-}$) is generated, and the generated oxide ion is discharged by an oxygen pumping action from the interior space 31 to the second atmosphere introduction path 52. Thus, the CPU uses the second electrochemical cell 12c to substantially eliminate oxygen contained in the test gas in the interior space 31.

The magnitude of the electrode current which flows between the third electrode 12a and the fourth electrode 12b (second oxygen decomposition current value) at this time corresponds to the concentration of oxygen contained in the test gas. The ECU receives a signal corresponding to the second oxygen decomposition current value outputted from the ammeter 71. Thus, the CPU used the second electrochemical cell 12c to detect the concentration of oxygen contained in the test gas in the interior space 31. And, based on the detected concentration of oxygen, the air-fuel ratio of the fuel-air mixture supplied to the internal combustion engine is computed.

On the other hand, the CPU applies, as the second predetermined voltage, a voltage at which the decomposition current of nitrogen oxide flows between the first electrode 11a and the second electrode 11b ($V_{SOx}$) (for instance, 1.1 V) so that the first electrode 11a and the second electrode 11b become a cathode and an anode, respectively, in a state where the element portion 10 is heated to a first predetermined temperature by the heater 41. As mentioned above, oxygen contained in the test gas in the interior space 31 is substantially eliminated by the second electrochemical cell 12c. Therefore, at the first electrode 11a, sulfur oxide contained in the test gas is decomposed, and an electrode current accompanying this flows between the first electrode 11a and the second electrode 11b.

However, as mentioned above, the SOx sensor shown in the present example detects the concentration of sulfur oxide in the test gas based on a phenomenon in which the magnitude of the decomposition current of water in the first electrochemical cell (sensor cell) on the downstream side changes according to the concentration of the sulfur oxide. Namely, in the first electrochemical cell 11c in the second state, not only sulfur oxide contained in the test gas, but also water contained in the test gas are decomposed. Therefore, the first electrode current detected in the first electrochemical cell 11c in the second state includes the decomposition current of sulfur oxide contained in the test gas (SOx decomposition current) and the decomposition current of water contained in the test gas (water decomposition current).

Figure 11:
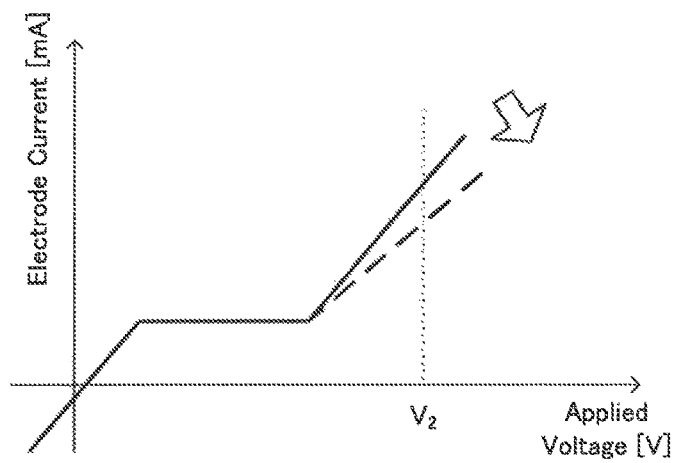
FIG. 11 is a schematic graph for explaining a phenomenon in which the higher the concentration of sulfur oxide contained in a test gas becomes, the smaller the first electrode current in the second state becomes, in a SOx sensor to which an abnormality diagnosis system of a gas sensor according to a third embodiment of the present disclosure (third system) is applied.

As shown by an outlined arrow in FIG. 11, the first electrode current when the first applied voltage is the second predetermined voltage (V2) becomes smaller, as the concentration of sulfur oxide contained in the test gas becomes higher. It is considered that this phenomenon is because sulfur oxide and water contained in the test gas are reductively decomposed in the first electrochemical cell 11c in the second state, and the decomposition product of sulfur oxide adsorbs to and accumulates on the first electrode 11a that is a cathode of the first electrochemical cell 11c.

Figure 12:
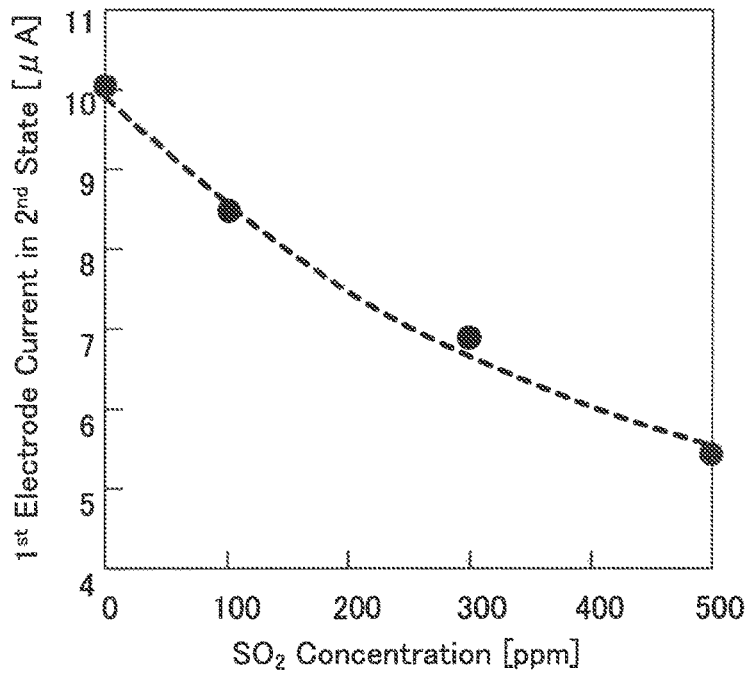
FIG. 12 is a graph obtained by plotting the first electrode current when the first applied voltage is the second predetermined voltage (V2) with respect to the concentration of sulfur oxide (in this case, sulfur dioxide ($SO_2$)) contained in a test gas, in the SOx sensor to which the third system is applied.

FIG. 12 is a graph obtained by plotting the first electrode current when the first applied voltage is the second predetermined voltage (V2) with respect to the concentration of sulfur oxide (in this case, sulfur dioxide ($SO_2$)) contained in a test gas. As apparent from FIG. 12, the first electrode current when the first applied voltage is the second predetermined voltage (V2) changes depending on the concentration of sulfur oxide (in this case, sulfur dioxide (SOx)) contained in a test gas. Therefore, based on the first electrode current when the first applied voltage is the second predetermined voltage (V2), the concentration of the sulfur oxide (in this case, sulfur dioxide (SOx)) contained in a test gas can be detected. In the present example, an abnormality diagnosis system of a gas sensor according to the present disclosure is applied to a SOx sensor which detects the concentration of sulfur oxide contained in a test gas based on such a measurement principle.

Similarly to the NOx sensor previously mentioned about the second system, also in a SOx sensor, by an abnormality diagnostic method of output characteristics of a gas sensor performed based on the magnitude of a decomposition current of oxygen which exists in a comparatively large amount in a test gas, a minute change of the output characteristics of the concentration of sulfur oxide which exists in a slight amount in an exhaust gas cannot be detected accurately and easily.

On the other hand, similarly to the second system, a third system diagnoses the existence of an abnormality of output characteristics of a SOx sensor, based on the magnitude of the decomposition current of water (water decomposition current value) whose decomposition starts at an applied voltage higher than that for oxygen, detected when fuel is supplied to the internal combustion engine.

However, when an applied voltage at which the reductive decomposition of water occurs is applied between the first electrode 11a and the second electrode 11b having the above-mentioned configurations, not only water, but also sulfur oxide contained in a test gas are decomposed reductively. The first predetermined temperature in the present example is 600° C., the decomposition product of sulfur oxide adsorbs to the first electrode 11a in the present example, as apparent from the above-mentioned explanation about measurement principle. Therefore, when detecting the decomposition current of water for the purpose of an abnormality diagnosis in the present example, it may be necessary to raise the temperature of the element portion 10 so that the decomposition product of sulfur oxide does not adsorb to the first electrode 11a. In the present example, when detecting the decomposition current of water for the purpose of an abnormality diagnosis, the temperature of the element portion 10 is set to 750° C.

Using SOx sensors with variously changed output characteristics, the output value (the first electrode current value in a second state) of the gas sensor and the water decomposition current value ($I_{H2O}$) detected by the second system, as for an exhaust gas containing a constant concentration (100 ppm) of sulfur oxide was measured, and the correlation between these investigated. In the first electrochemical cell 11c, the first electrode current value in the second state is detected at the temperature of the element portion 10 set as 600° C. and the first applied voltage set as 1.1 V, and the decomposition current of water ($I_{H2O}$) is detected at the temperature of the element portion 10 set as 750° C. and the first applied voltage set as 1.0 V.

Figure 13:
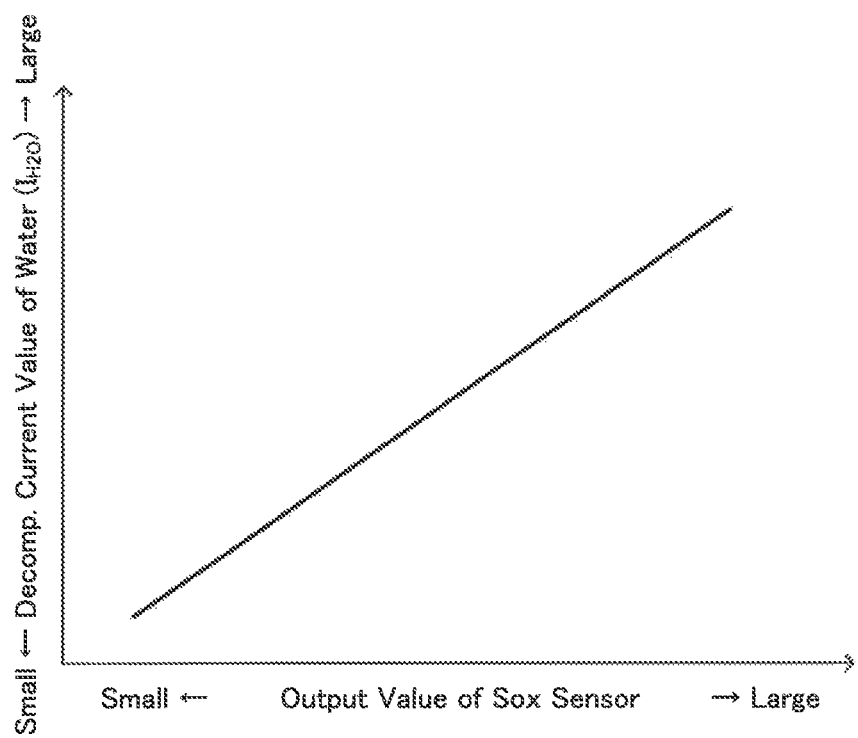
FIG. 13 is a schematic graph for showing a correlation between the output value from the SOx sensor and the decomposition current value of water ($I_{H2O}$) detected in the abnormality diagnosis by the second system.

As shown in FIG. 13, the output value (first electrode current value in the second state) of a SOx sensor and the water decomposition current value ($I_{H2O}$) which were acquired by the above-mentioned experiment showed a correlation. This shows that the water decomposition current value ($I_{H2O}$) used for an abnormality diagnosis of a gas sensor by the third system is suitable also as an index for diagnosing an abnormality of the output characteristics of a SOx sensor.

Here, an abnormality diagnostic operation of a gas sensor (SOx sensor) performed by the third system will be explained. In addition, in the present example, similarly to the exemplification of the second system, the air-fuel ratio of the fuel-air mixture supplied to the internal combustion engine is detected by the gas sensor, and the reference water decomposition current value specified from the air-fuel ratio may not be used as it is, and the reference water decomposition current value is corrected based on the decomposition current value of oxygen detected at the time of the execution of a fuel cut (FC). Furthermore, in the present example, when the decomposition current value of oxygen detected at the time of the FC execution has largely deviated from a reference value, it is judged that the gas sensor is abnormal, and the abnormality diagnosis of the gas sensor based on the water decomposition current value may not be performed.

The abnormality diagnosis of the gas sensor based on the decomposition current value of oxygen (atmosphere decomposition current value) detected during the FC execution (FC diagnosis) is the same as the FC diagnosis of the gas sensor (NOx sensor) performed by the second system which has been explained while referring to FIG. 9. Therefore, an explanation about the FC diagnosis of the gas sensor (SOx sensor) performed by the third system is omitted.

Figure 14:
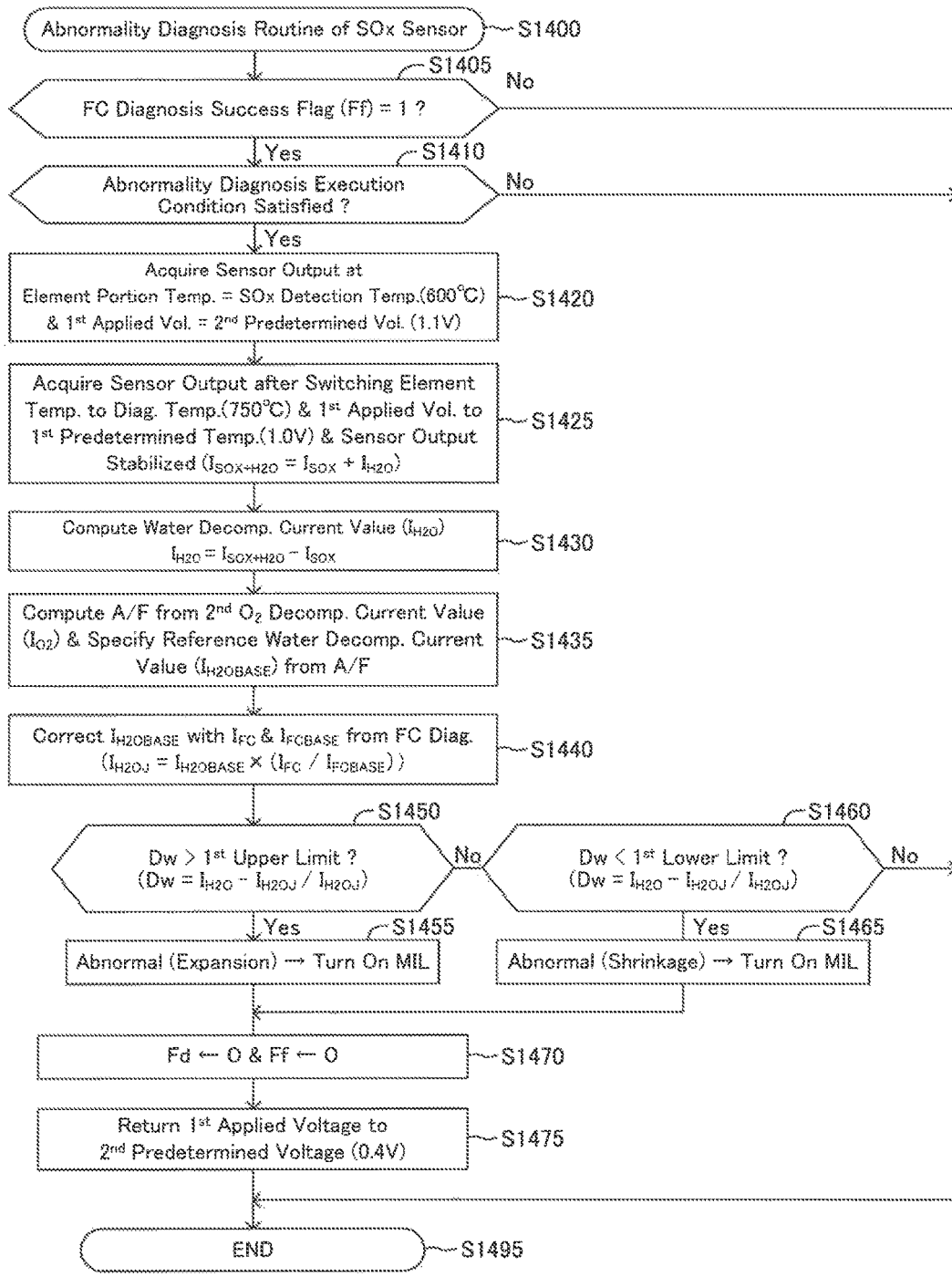
FIG. 14 is a flowchart for showing an example of an abnormality diagnostic operation of a gas sensor, which is performed by the third system.

Next, the abnormality diagnosis of the gas sensor based on the water decomposition current value performed by the third system will be explained. FIG. 14 is a flowchart for showing an example of the abnormality diagnosis routine of the gas sensor (SOx sensor) performed by the third system. Each step contained in the flowchart shown in FIG. 14 corresponds to each step contained in the flowchart shown in FIG. 10, and the last two figures of the numbers of the corresponding steps in respective figures are the same. First, the CPU which the above-mentioned ECU comprises starts treatments from step S1400 at a predetermined timing, and progresses to step S1405.

The flow of the treatments from step S1405 is the same as the flow of the treatments from step S1005 included in the flowchart shown in FIG. 10, except for the following three points:

(x) The test gas component used as the subject for detection is sulfur oxide in FIG. 14 while it is nitrogen oxide in FIG. 10. (y) In step S1420 of FIG. 14 corresponding to step S1020 of FIG. 10, a sensor output is acquired at the element portion temperature set as a temperature for detecting SOx (600° C.) and the first applied voltage set as the second predetermined voltage (1.1 V). (z) In the following step S1425 (corresponding to step S1025), not only the first applied voltage, but also the temperature of the element portion 10 are changed, in order to acquire the water decomposition current value.

Therefore, although the treatment performed in each step was explained in detail while referring to FIG. 10 as for the second system, in the present example, each of respective steps contained in the flowchart shown in FIG. 10 is not explained here.

As explained above, in accordance with the third system, in a limited-current type oxygen sensor (SOx sensor) which detects the decomposition current value of sulfur oxide contained in an exhaust gas of an internal combustion engine, the decomposition current value of water ($H_2O$) (water decomposition current) is detected and, based on its deviation from the reference decomposition current value of water (reference water decomposition current) corresponding to the concentration of water contained in the exhaust gas, the existence of an abnormality of output characteristics of the limited-current type gas sensor is diagnosed. Thereby, not only a remarkable abnormality, but also a minute abnormality, of the output characteristics of the gas sensor, can be diagnosed accurately and easily.

In addition, although the air-fuel ratio of the fuel-air mixture supplied to an internal combustion engine is detected by the gas sensor, and the reference water decomposition current value specified from the air-fuel ratio is corrected based on the decomposition current value of oxygen, which is detected at the time of the fuel cut, also in the present example, the reference water decomposition current value may be used as it is, without correcting the reference water decomposition current value. Alternatively, as mentioned above, the reference water decomposition current value may be specified from the concentration of water contained in the test gas, which is detected by a separately prepared humidity sensor, etc. Furthermore, for example, the concentration of water contained in the test gas may be estimated based on the temperature of the intake air to the internal combustion engine, and the reference water decomposition current value may be specified from this estimated concentration of water. In addition, when judged that the output characteristics of the gas sensor is normal, the second reference atmosphere decomposition current value ($I_{FCBASE}$) may be updated (learned) with the second atmosphere decomposition current value ($I_{FC}$) acquired in the above-mentioned FC diagnosis.

In the present example, the water decomposition current value ($I_{H2O}$) which is the magnitude of the electrode current which flows due to the decomposition of water in the first state was computed by subtracting the SOx decomposition current value ($I_{SOX}$) from the first electrode current value ($I_{SOX+H2O}$). However, the concentration of sulfur oxide contained in a test gas (ppm order) is sufficiently small as compared with the concentration of water contained in the test gas (% order). Therefore, the first electrode current value ($I_{SOX+H2O}$) may be used as the water decomposition current value ($I_{H2O}$) as it is.

As mentioned above, although some embodiments and modifications which have specific configurations have been explained, sometimes referring to the accompanying drawings, for the purpose of explaining the present invention, it should not be interpreted that the scope of the present invention is limited to these exemplary embodiments and modifications, and it is needless to say that any modifications can be properly added within the limits of the matter described in the claims and the specification.

REFERENCE SIGNS LIST 10, 20 and 30: Element Portion, 11a, 12a and 13a: Electrode (Cathode), 11b, 12b and 13b: Electrode (Anode), 11s and 12s: First and Second Solid-electrolyte Object, 11c, 12c and 13c: Pumping Cell (First to Third Electrochemical Cell), 21a, 21b, 21c, 21d, 21e and 21f: First to Sixth Alumina Layer, 31: Interior Space, 32: Diffusion-resistance Object, 41: Heater, 51 and 52: First and Second Atmosphere Introduction Path, 61, 62 and 63: Power Supply, 71, 72 and 73: Ammeter, and 81: Current Difference Detector Circuit.

The invention claimed is:

1. An abnormality diagnosis system of a gas sensor for diagnosing whether a gas sensor is abnormal, comprising:
   an element portion comprising a first electrochemical cell, the first electrochemical cell including
   a solid-electrolyte object with oxide ion conductivity, and a first electrode and second electrode respectively formed on the surface of the solid-electrolyte object;
   a gas impermeable portion; and
   a diffusion-resistance portion,
   the element portion being configured so that an exhaust gas of an internal combustion engine as a test gas is introduced into an interior space defined by said solid-electrolyte object, said gas impermeable portion, and said diffusion-resistance portion through said diffusion-resistance portion, wherein said first electrode is exposed to said interior space, and said second electrode is exposed to a space other than said interior space;
   a heater which heats said element portion when energized;
   a voltage-control portion which changes a first applied voltage, wherein the first applied voltage is a voltage applied between said first electrode and said second electrode;
   a temperature adjustment portion which changes the temperature of said element portion by controlling amount of energization of said heater; and
   a measurement control portion which controls said first applied voltage using said voltage-control portion, controls the temperature of said element portion using said temperature adjustment portion, and acquires a first electrode current value, the first electrode current value being a value of a current flowing between said first electrode and said second electrode.

2. The system of claim 1,
   wherein said first electrode is configured to decompose water contained in said test gas, in a first state where the temperature of said element portion is a first predetermined temperature which is not lower than an activation temperature,
   wherein the activation temperature is a temperature at which said solid-electrolyte object expresses oxide ion conductivity,
   wherein said first applied voltage is a first predetermined voltage falling within a predetermined first voltage zone, and
   wherein said first electrode is further configured to decompose a test component containing an oxygen atom in its molecular structure and contained in said test gas, in a second state where the temperature of said element portion is said first predetermined temperature and said first applied voltage is a second predetermined voltage falling within a predetermined second voltage zone, and
   wherein said measurement control portion is configured to acquire the first electrode current value acquired in the second state as a test component concentration-related value which is a value associated with the concentration of said test component contained in said test gas.

3. The system of claim 2,
   wherein said measurement control portion has previously memorized a first correspondence relation,
   wherein the first correspondence relation describes a correspondence relation of a moisture-related value with a reference water decomposition current value,
   wherein the moisture-related value is a value corresponding to the concentration of water contained in said test gas, and
   wherein the reference water decomposition current value is a value of a current flowing between said first electrode and said second electrode due to the decomposition of water contained in said gas when said first electrochemical cell of said gas sensor in a normal state is in said first state.

4. The system of claim 3,
   wherein said measurement control portion is configured to acquire said moisture-related value at present,
   specify a reference water decomposition current value corresponding to said acquired moisture-related value, based on said first correspondence relation, and
   acquire a water decomposition current value which is a value of a current flowing between said first electrode and said second electrode due to the decomposition of water contained in said test gas, based on said first electrode current value acquired in said first state, when fuel is supplied to said internal combustion engine, and
   wherein said measurement control portion is configured to judge that said gas sensor is abnormal, when a moisture detection deviation is larger than a predetermined first upper limit, or when said moisture detection deviation is smaller than a predetermined first lower limit,
   the moisture detection deviation being a ratio of a value obtained by subtracting said specified reference water decomposition current value from said water decomposition current value to said specified reference water decomposition current value.

5. The abnormality diagnosis system according to claim 4, wherein:
   said first electrode is configured to decompose oxygen as the test component contained in the test gas in the second state where the first applied voltage is in the second voltage zone lower than the first voltage zone, and
   said measurement control portion is configured to acquire a first oxygen decomposition current value, the first oxygen decomposition current value being a value of a current flowing between the first electrode and the second electrode due to the decomposition of oxygen contained in the test gas, based on the test component concentration-related value acquired in the second state, where the first applied voltage is in the second voltage zone lower than the first voltage zone.

6. The abnormality diagnosis system according to claim 5, wherein:
said measurement control portion further comprises a humidity sensor that detects the concentration of water contained in said test gas,
said measurement control portion is configured to acquire said detected concentration of water as said moisture-related value, and
said measurement control portion has previously memorized said first correspondence relation in which the concentration of water detected by said humidity sensor is used as said moisture-related value.

7. The abnormality diagnosis system according to claim 5, wherein:
said measurement control portion is configured to acquire said acquired first oxygen decomposition current value as said moisture-related value, and has previously memorized said first correspondence relation in which said first oxygen decomposition current value acquired when said first electrochemical cell of said gas sensor in a normal state is in said second state is used as said moisture-related value.

8. The abnormality diagnosis system according to claim 7, wherein:
said measurement control portion has previously memorized a first reference atmosphere decomposition current value,
said measurement control portion is configured to acquire the first atmosphere decomposition current value, and
said measurement control portion is configured to correct said specified reference water decomposition current value based on a ratio of said acquired first atmosphere decomposition current value to said first reference atmosphere decomposition current value, wherein
the first reference atmosphere decomposition current value is a value of a current flowing between said first electrode and said second electrode due to the decomposition of oxygen contained in said test gas when fuel is not supplied to said internal combustion engine and said first electrochemical cell of said gas sensor in a normal state is in said second state, and
the first atmosphere decomposition current value, which is a value of a current flowing between said first electrode and said second electrode due to the decomposition of oxygen contained in said test gas based on said first electrode current value acquired in said second state when fuel, is not supplied to said internal combustion engine.

9. The abnormality diagnosis system according to claim 8, wherein:
said measurement control portion is configured to judge that said gas sensor is abnormal, when a first atmosphere detection deviation is larger than a predetermined second upper limit, or when said first atmosphere detection deviation is smaller than a predetermined second lower limit,
wherein the first atmosphere detection deviation is a ratio of a value obtained by subtracting said first reference atmosphere decomposition current value from said acquired first atmosphere decomposition current value to said first reference atmosphere decomposition current.

10. The abnormality diagnosis system according to claim 4, wherein:
said element portion further comprises
a second electrochemical cell including said solid-electrolyte object or another solid-electrolyte object other than said solid-electrolyte object, and a third electrode and fourth electrode respectively formed on the surface of the solid-electrolyte object,
wherein said third electrode is exposed to said interior space and said fourth electrode is exposed to a space other than said interior space, and
said third electrode is formed in a location nearer to said diffusion-resistance portion than said first electrode, and wherein
said voltage-control portion is configured to apply a second applied voltage between said third electrode and said fourth electrode,
said third electrode is configured to decompose oxygen contained in said test gas in a third state where the temperature of said element portion is said first predetermined temperature and said second applied voltage is applied, and to discharge the oxygen from said interior space,
said first electrode is configured to decompose nitrogen oxide as said test component contained in said test gas in said second state where said first applied voltage is in said second voltage zone lower than said first voltage zone, and
said measurement control portion is configured to acquire a NOx decomposition current value, based on said test component concentration-related value acquired in said second state where said first applied voltage is in said second voltage zone lower than said first voltage zone, wherein the NOx decomposition current value is a value of a current flowing between said first electrode and said second electrode due to the decomposition of nitrogen oxide contained in said test gas.

11. The abnormality diagnosis system according to claim 10, wherein:
said measurement control portion further comprises a humidity sensor that detects the concentration of water contained in said test gas,
is configured to acquire said detected concentration of water as said moisture-related value, and
has previously memorized said first correspondence relation in which the concentration of water detected by said humidity sensor is used as said moisture-related value.

12. The abnormality diagnosis system according to claim 10, wherein:
said measurement control portion is configured to
acquire a second oxygen decomposition current value which is a value of a current flowing between said third electrode and said fourth electrode due to the decomposition of oxygen contained in said test gas in said third state, and
acquire said acquired second oxygen decomposition current value as said moisture-related value, and
has previously memorized said first correspondence relation in which said second oxygen decomposition current value acquired when said second electrochemical cell of said gas sensor in a normal state is in said third state is used as said moisture-related value.

13. The abnormality diagnosis system according to claim 12, wherein:
said measurement control portion
has previously memorized a second reference atmosphere decomposition current value, wherein the second reference atmosphere decomposition current value is a value of a current flowing between said third electrode and said fourth electrode due to the decomposition of oxygen contained in said test gas when fuel is not supplied to said internal combustion engine and said second electrochemical cell of said gas sensor in a normal state;
is in said third state, and
is configured to;
acquire a second atmosphere decomposition current value, which is a value of a current flowing between said third electrode and said fourth electrode due to the decomposition of oxygen contained in said test gas based on said second oxygen decomposition current value acquired in said third state when fuel is not supplied to said internal combustion engine, and
correct said specified reference water decomposition current value based on a ratio of said second atmosphere decomposition current value to said second reference atmosphere decomposition current value.

14. The abnormality diagnosis system according to claim 13, wherein:
said measurement control portion is configured to judge that said gas sensor is abnormal, when a second atmosphere detection deviation which is a ratio of a value obtained by subtracting said second reference atmosphere decomposition current value from said acquired second atmosphere decomposition current value to said second reference atmosphere decomposition current value is larger than a predetermined third upper limit, or
when said second atmosphere detection deviation is smaller than a predetermined third lower limit.

15. The abnormality diagnosis system according to claim 4, wherein:
said element portion further comprises
a second electrochemical cell including said solid-electrolyte object or another solid-electrolyte object other than said solid-electrolyte object and a third electrode and fourth electrode respectively formed on the surface of the solid-electrolyte object,
is configured so that said third electrode is exposed to said interior space and said fourth electrode is exposed to a space other than said interior space, and
said third electrode is formed in a location nearer to said diffusion-resistance portion than said first electrode, and wherein
said voltage-control portion is configured also to apply a second applied voltage between said third electrode and said fourth electrode,
said third electrode is configured to decompose oxygen contained in said test gas in a third state where the temperature of said element portion is said first predetermined temperature and said second applied voltage is applied, and to discharge the oxygen from said interior space,
said first electrode is configured to decompose sulfur oxide as said test component contained in said test gas in said second state, and
said measurement control portion is configured to acquire a SOx decomposition current value based on said test component concentration-related value acquired in said second state, wherein the SOx decomposition current value is a value of a current flowing between said first electrode and said second electrode due to the decomposition of sulfur oxide contained in said test gas.

16. The abnormality diagnosis system according to claim 4, wherein:
said measurement control portion is configured to maintain the temperature of said element portion at a second predetermined temperature using said temperature adjustment portion, when acquiring a water decomposition current value in said first state, in a case where said first electrode can decompose sulfur oxide contained in said test gas in said first state,
wherein the second predetermined temperature is a temperature not less than said activation temperature and a temperature at which a desorption rate, that is a velocity at which a decomposition product of sulfur oxide contained in said test gas desorbs from said first electrode, is larger than an adsorption rate, that is a velocity at which the decomposition product adsorbs to said first electrode.

* * * * *